US011989803B2

(12) United States Patent
Behrooz

(10) Patent No.: US 11,989,803 B2
(45) Date of Patent: May 21, 2024

(54) SYSTEMS AND METHODS FOR 3D RECONSTRUCTION OF ANATOMICAL ORGANS AND INCLUSIONS USING SHORT-WAVE INFRARED (SWIR) PROJECTION TOMOGRAPHY

(71) Applicant: PerkinElmer Health Sciences, Inc., Waltham, MA (US)

(72) Inventor: Ali Behrooz, Waltham, MA (US)

(73) Assignee: PerkinElmer Health Sciences, Inc., Waltham, MA (US)

( * ) Notice: Subject to any disclaimer, the term of this patent is extended or adjusted under 35 U.S.C. 154(b) by 0 days.

(21) Appl. No.: 16/339,445

(22) PCT Filed: Mar. 30, 2018

(86) PCT No.: PCT/US2018/025393
§ 371 (c)(1),
(2) Date: Apr. 4, 2019

(87) PCT Pub. No.: WO2019/190549
PCT Pub. Date: Oct. 3, 2019

(65) Prior Publication Data
US 2021/0327107 A1    Oct. 21, 2021

(51) Int. Cl.
*G06T 11/00* (2006.01)
*A61B 5/00* (2006.01)

(52) U.S. Cl.
CPC .......... *G06T 11/006* (2013.01); *A61B 5/0073* (2013.01); *A61B 5/704* (2013.01); *G06T 11/005* (2013.01); *A61B 2503/40* (2013.01)

(58) Field of Classification Search
CPC ... G06T 11/006; G06T 11/005; A61B 5/0073; A61B 5/704; A61B 2503/40;
(Continued)

(56) References Cited

U.S. PATENT DOCUMENTS 7,778,392 B1 *  8/2010  Berman .................. A61B 6/032
                                              378/4
8,909,326 B2 * 12/2014  Stearns .............. A61K 49/0013
                                              600/407
(Continued)

FOREIGN PATENT DOCUMENTS

CN       101634748 A      1/2010
CN       102023148 A      4/2011
(Continued)

OTHER PUBLICATIONS

Hartwig et al. "First Prototype of a Near Infrared Tomography for Mapping the Myocardial Oxygenation in Small Animal Isolated hearts". IEEE International Workshop on Imaging, Systems and Techniques—IST 2008, Chania, Greece, Sep. 10-12, 2008.
(Continued)

*Primary Examiner* — Joseph M Santos Rodriguez
*Assistant Examiner* — Amy Shafqat
(74) *Attorney, Agent, or Firm* — Banner & Witcoff, Ltd.

(57) ABSTRACT

Presented herein are systems and methods for tomographic imaging of a region of interest in a subject using short-wave infrared light to provide for accurate reconstruction of absorption maps within the region of interest. The reconstructed absorption maps are representations of the spatial variation in tissue absorption within the region of interest. The reconstructed absorption maps can themselves be used to analyze anatomical properties and biological processes within the region of interest, and/or be used as input information about anatomical properties in order to facilitate data processing used to obtain images of the region of interest via other imaging modalities. For example, the reconstructed absorption maps may be incorporated into forward models that are used in tomographic reconstruction processing in fluorescence and other contrast-based tomographic imaging modalities. Incorporating reconstructed absorption maps
(Continued)

into other tomographic reconstruction processing algorithms in this manner improves the accuracy of the resultant reconstructions.

19 Claims, 6 Drawing Sheets

(58) Field of Classification Search
CPC ... A61B 5/0035; A61B 5/0075; A61B 5/0062; A61B 5/0071; A61B 2560/0223; G01B 11/24; G01N 21/35; G01N 2021/1787
See application file for complete search history.

(56) References Cited

U.S. PATENT DOCUMENTS

| | | | | |
|---|---|---|---|---|
| 2004/0247076 | A1* | 12/2004 | Navab | A61B 5/0059 378/63 |
| 2004/0249260 | A1* | 12/2004 | Wang | A61B 6/508 600/407 |
| 2006/0173354 | A1* | 8/2006 | Ntziachristos | A61B 5/0071 600/476 |
| 2006/0249689 | A1* | 11/2006 | Eustergerling | A61B 5/0059 250/458.1 |
| 2007/0238957 | A1* | 10/2007 | Yared | A61B 5/0035 600/407 |
| 2007/0258122 | A1 | 11/2007 | Champgoulov et al. | |
| 2010/0022866 | A1* | 1/2010 | Feke | A61B 6/4417 600/407 |
| 2012/0196320 | A1 | 8/2012 | Seibel et al. | |
| 2012/0265050 | A1 | 10/2012 | Wang | |
| 2016/0038029 | A1 | 2/2016 | Darne et al. | |
| 2016/0377545 | A1* | 12/2016 | Wang | G01N 21/6456 250/459.1 |
| 2017/0200271 | A1* | 7/2017 | Atria | A61B 6/032 |
| 2018/0053298 | A1* | 2/2018 | Mahadevan-Jansen | G06T 7/0012 |
| 2018/0175582 | A1* | 6/2018 | Rothberg | H01S 3/025 |
| 2018/0180550 | A1* | 6/2018 | Franjic | G01N 21/474 |

FOREIGN PATENT DOCUMENTS

| | | |
|---|---|---|
| CN | 105894537 A | 8/2016 |
| DE | 4445214 A1 | 6/1996 |
| DE | 20010250 U1 | 12/2000 |
| EP | 0329115 A1 | 8/1989 |
| EP | 0559978 A1 | 9/1993 |
| EP | 0905509 A1 | 3/1999 |
| EP | 0988060 A2 | 3/2000 |
| EP | 1018747 A2 | 7/2000 |
| EP | 1113822 A1 | 7/2001 |
| EP | 1181940 A2 | 2/2002 |
| EP | 1237583 A1 | 9/2002 |
| EP | 0796111 B1 | 4/2003 |
| EP | 1065250 B1 | 12/2004 |
| EP | 1480683 A2 | 12/2004 |
| EP | 1679082 A1 | 7/2006 |
| EP | 1833513 A1 | 9/2007 |
| EP | 1968431 A2 | 9/2008 |
| WO | 96/17628 A1 | 6/1996 |
| WO | 97/40104 A1 | 10/1997 |
| WO | 98/47538 A2 | 10/1998 |
| WO | 99/51702 A1 | 10/1999 |
| WO | 00/16810 A1 | 3/2000 |
| WO | 01/21624 A1 | 3/2001 |
| WO | 01/43781 A1 | 6/2001 |
| WO | 01/95795 A2 | 12/2001 |
| WO | 03/074091 A2 | 9/2003 |
| WO | 03/102558 A1 | 12/2003 |
| WO | 2004/008123 A1 | 1/2004 |
| WO | 2004/072906 A1 | 8/2004 |
| WO | 2004/081865 A2 | 9/2004 |
| WO | 2005/040769 A2 | 5/2005 |
| WO | 2005/089637 A2 | 9/2005 |
| WO | 2006/020896 A3 | 5/2006 |
| WO | 2006/062895 A2 | 6/2006 |
| WO | 2006/063246 A1 | 6/2006 |
| WO | 2007/072085 A1 | 6/2007 |
| WO | 2007/072580 A1 | 6/2007 |
| WO | 2007/089641 A3 | 2/2008 |
| WO | 2007/111669 A3 | 2/2008 |
| WO | 2011/025950 A2 | 3/2011 |

OTHER PUBLICATIONS

Oct. 19, 2021 (EP)—Extended European Search Report Application No. 18912501.6.
Ntziachristos, et al. MRI-Guided Diffuse Optical Spectroscopy of Malignant and Benign Breast Lesions. Neoplasia. vol. 4. 347-354. 2002.
Ntziachristos et al. Concurrent MRI and diffuse optical tomography of breast after indocyanine green enhancement. PNAS. vol. 97. No. 6. 2767-2772. Mar. 14, 2000.
Ntziachristos et al. Multichannel photon counting instrument for spatially resolved near infrared spectroscopy. Review of Scientific Instruments. vol. 70. No. 1. 193-201. Jan. 1999.
O'Leary et al. Experimental images of heterogeneous turbid media by frequency-domain diffusing-photon tomography. Optics Letters. 426-428. Oct. 31, 1994.
Ozmen et al. Infrared fluorescence sensing of submicromolar calcium: pushing the limits of photoinduced electron transfer. Tetrahedron Letters. vol. 41. 9185-9188. Sep. 26, 2000.
Rajadhyaksha et al. In Vivo Confocal Scanning Laser Microscopy of Human Skin: Melanin Provides Strong Contrast. 946-952. 1995.
Rasmussen et al. Relative transport in fluorescence-enhanced frequency domain photon migration. Medical Physics. vol. 33. No. 12. 4685-4700. Dec. 2006.
Ripoll et al. Boundary conditions for light propagation in diffusive media with nonscattering regions. J. Opt. Soc. Am. A. vol. 17. No. 9. 1671-1681. Sep. 2000.
Ripoll et al. Effect of roughness in nondiffusive regions within diffusive media. J. Opt. Soc. Am. A. vol. 18. No. 4. 940-947. Apr. 2001.
Ripoll et al. Free-Space Propagation of Diffuse Light: Theory and Experiments. Physical Review Letters. vol. 91. No. 10. 1-4. Sep. 5, 2003.
Ripoll et al. Non-Contact Diffuse Optical Tomography. Proc. of SPIE. vol. 5474. 215-223. 2003.
Ripoll et al. Recovery of optical parameters in multiple-layered diffusive media: theory and experiments. J. Opt. Soc. Am. A. vol. 18. No. 4. 821-830. Apr. 2001.
Ripoll et al. Reflection and transmission coefficients for diffuse photon density waves. Optic Letters. vol. 24. No. 12. 796-798. Jun. 15, 1999.
Saggau, Peter. New methods and uses for fast optical scanning. ESCONU. vol. 16. No. 5. 543-550. Oct. 2006.
Schulz et al. Experimental Fluorescence Tomography of Tissues With Noncontact Measurements. vol. 23. No. 4. 492-500. Apr. 2004.
Schweiger et al. Optical tomographic reconstruction in a complex head model using a priori region boundary information. Phys. Med. Biol. vol. 44. 2703-2721. Apr. 6, 1999.
Shaner et al. A guide to choosing fluorescent proteins. Nature Methods. vol. 2. No. 12. 905-909. Dec. 2005.
Shaner et al. Improved monomeric red, orange and yellow fluorescent proteins derived from Discosoma sp. Red fluorescent protein. Nature Biotechnology. vol. 22. No. 12. 1567-1572. Dec. 2004.
Shi et al. Transmission in near-infrared optical windows for deep brain imaging. J. Biophotonics. vol. 9. No. 1-2. 39-43. Nov. 11, 2015.
Soubret et al. Accuracy of Fluorescent Tomography in the Presence of Heterogeneities: Study of the Normalized Born Ratio. Transactions on Medical Imaging. vol. 24. No. 10. 1377-1386. Oct. 2005.
Tearney et al. In Vivo Endoscopic Optical biopsy with Optical Coherence Tomography. Science. vol. 276. 2037-2039. Jun. 27, 1997.
Tsien, Roger. The Green Fluorescent Protein. Annu. Rev. Biochem 67:509-544. 1998.

(56) References Cited

OTHER PUBLICATIONS

Tung et al. In Vivo Imaging of Proteolytic Enzyme Activity Using a Novel Molecular Reporter. 4953-4958. Sep. 1, 2001.
Tyagi et al. Molecular Beacons: Probes that Fluoresce upon Hybridization. Nature Biotechnology. vol. 14. 303-308. Mar. 1996.
Tyagi et al. Multicolor molecular beacons for allele discrimination. Nature Biotechnology. vol. 16. 49-53. Jan. 1998.
Tyagi et al. Wavelength-shifting molecular beacons. Nature Biotechnology. vol. 18. 1191- 1196. Nov. 2000.
Weissleder et al. A. In vivo imaging of tumors with protease-activated near-infrared fluorescent probes. Nature Biotechnology. vol. 17. 375-378. Apr. 1999.
Weissleder et al. In vivo magnetic resonance imaging of transgene expression. Nature Medicine. vol. 6. No. 3. 351-355. Mar. 2000.
Wu et al. Fluorescence tomographic imaging in turbid media using early-arriving photons and Laplace transforms. Proceedings of the National Academy of Sciences of the United States of America. vol. 94. No. 16. 8783-8788. Aug. 5, 1997.
Yaghjian, Arthur. Electric Dyadic Green's Functions in the Source Region. vol. 68. No. 2. 248-263. Feb. 1980.
Zhang et al. Coregistered tomographic x-ray and optical breast imaging: initial results. Journal of Biomedical Optics. vol. 10. No. 2. 024033:2-024033:9. Apr. 13, 2005.
Zhang et al. Creating New Fluorescent Probes for Cell Biology. Molecular Cell Biology. 906-918. Dec. 2002.
Jun. 11, 2018—ISR & WO—PCT/US18/25393.
Provisional U.S. Appl. No. 60/460,086.
Dec. 16, 2013 (WO) ISR & WO—PCT/US2013/065107.
Dec. 17, 2015 (EP)—Opposition to Patent—EP 1968431.
Achilefu et al. Novel Receptor-Targeted Fluorescent Contrast Agents for in Vivo Tumor Imaging. Investigative Radiology. vol. 35. Issue 8. 479-485. May 11, 2000.
Baird et al. Biochemistry, mutagenesis, and oligomerization of DsRed, a red fluorescent protein from coral. PNAS. vol. 97. No. 22. 11984-11989.
Ballou et al. Fluorescence Imaging of Tumors In Vivo. Current Medicinal Chemistry. 795-805. 2005.
Ballou et al. Tumor Detection and Visualization Using Cyanine Fluorochrome-Labeled Antibodies. Biotechnol. Prog. 649-658. 1997.
Becker et al. Receptor-targeted optical imaging of tumors with near-infrared fluorescent ligands. Nature Biotechnology. 327-331. Apr. 2001.
Behrooz et al. Hadamard multiplexed fluorescence tomography. OSA. 763-777. Feb. 18, 2014.
Beuthan, Juergen. Optical diagnostics—State of the art. Medical Laser Applcaition. vol. 20. 131-134. Mar. 11, 2005.
Boas et al. Scattering and Imaging with Diffusing Temporal Field Correlations. Physical Review Letters. vol. 75. No. 9. 1855-1858. Aug. 28, 1995.
Bogdanov et al. The development of in vivo imaging systems to study gene expression. Tibtech. vol. 16. 1-6. Jan. 1998.
Bremer et al. In Vivo molecular target assessment of matrix metalloproteinase inhibition. Nature Medicine. vol. 7. No. 6. 743-748. Jun. 2001.
Brukilacchio et al. Diffuse Optical Tomography System Combined With X-Ray Mammography for Improves Breast Cancer Detection. 1-220. May 2003.
Bugaj et al. Novel fluorescent contrast agents for optical imaging of in vivo tumors based on a receptor-targeted dye-peptide conjugate platform. Journal of Biomedical Optics. vol. 6. No. 2. 122-133. Apr. 2001.
Campbell et al. A monomeric red fluorescent protein. PMAS. vol. 99. No. 12. 7877-7882. Jun. 11, 2002.
Campo et al. Polymeric Photosensitizer Prodrugs for Photodynamic Therapy. Photochemistry and Photobiology. vol. 83. 958-965. Feb. 13, 2007.
Chance, Britton. Near-Infrared Images Using Continuous, Phase-Modulated, and Pulsed Light with Quantitation of Blood and Blood Oxygenation. 29-45.

Cubitt et al. Understanding, improving and using green fluorescent proteins. Elsevier Science Ltd. 448-455. Nov. 1995.
Davis et al. Magnetic resonance-coupled fluorescence tomography scanner for molecular imaging of tissue. Review of Scientific Instruments. vol. 79. No. 064302. 1-10. 2008.
Dehghani et al. Development of Hybrid NIR/MRI Imaging System Algorithm: Use of A-Priori Information for Tumor Detection in the Female Breast. 657-660.2002.
Dellian et al. Vascular permeability in a human tumour xenograft molecular charge dependence. British Journal of Cancer. vol. 82. No. 9. 1513-1518. Dec. 20, 1999.
Fiber laser. Wikipedia. Jun. 25, 2017 Retrieved from https://en.wikipedia.org/wiki/Fiber_laser.
Fischer et al. Basic Optics and Optical System Specifications. 17. 2008.
Gaudette et al. A comparison study of linear reconstruction techniques for diffuse optical tomographic imaging of absorption coefficient. Phys. Med. Biol. vol. 45. 1051-1070. 2000.
Gehrke et al. Application of Conventional- and Dual-Energy X-Ray Tomography in Process Engineering. Sensors Journal. vol. 5. No. 2. 183-187. Apr. 2005.
Gibson et al. Recent advances in diffuse imaging. Physics in Medicine and Biology. vol. 50. R1-R43. Feb. 2, 2005.
Giepmans et al. The Fluorescent Toolbox for Assessing Protein Location and Function. vol. 312. Science. 217-224. Apr. 14, 2006.
Goertzen et al. Simultaneous molecular and anatomical imaging of the mouse in vivo. Phys. Med. Biol. vol. 47. 4315-4328. Dec. 3, 2002.
Gurfinkel et al. Pharmacokinetics of ICG and HPPH-car for Detection of Normal and Tumor Tissue Using Fluorescence, Near-Infrared Continuous Wave Imaging. 245-248.
Guven et al. Diffuse optical tomography with a priori anatomical information. Phys. Med. Biol. vol. 50. 2837-2858. 2005.
Hawrysz et al. Developments Toward Diagnostic Breast Cancer Imaging Using Near-Infrared Optical Measurements and Fluorescent Contrast Agents. Neoplasia. vol. 2. No. 5. 388-417. Oct. 10, 2000.
Hecht, Jeff. Fiber Lasers: Fiber lasers: The state of the art. 1-11. Apr. 1, 2012.
Heikai et al. Molecular spectroscopy and dynamics of intrinsically fluorescent proteins: Coral red (dsRed) and yellow (Citrine). PNAS. vol. 97. No. 22. 11996-12001. Sep. 11, 2000.
Heim et al. Engineering green fluorescent protein for improved brightness, longer wavelengths and fluorescence resonance energy transfer. Current Biology. vol. 6. 178-182. Nov. 29, 1995.
Heim et al. Wavelength mutations and posttranslational autoxidation of green fluorescent protein. Proc. Natl. Acad. Sci. USA. vol. 91. 12501-12504. Aug. 19, 1994.
Hwang et al. A Multimode Optical Imaging System for Preclinical Application In Vivo: Technology Development, Multiscale Imaging, and Chemotherapy Assessment. Molecular Imaging and Biology. 432-442. Aug. 27, 2011.
Inoue et al. In vivo fluorescence imaging of the reticuloendothelial system using quantum dots in combination with bioluminescent tumor monitoring. Eur J Nucl Med Mol Imaging. vol. 34. 2048-2056. Sep. 21, 2007.
Kak et al. Principles of Computerized Tomographic Imaging. The Institute of Electrical and Electronics Engineers, Inc. 208-218.
Kundu et al. Tri-modality Small Animal Imaging System. 3863-3867.2004.
Li et al. Tomographic optical breast imaging guided by three-dimensional mammography. Applied Optics. vol. 42. No. 25. 5181-5190. Sep. 1, 2003.
Liao et al. A Three-Dimensional Registration Method for MicoUS/MicroPET Multimodality Small-Animal Imaging. 2-13. XP008108237.
Macaskill et al. Iterative approach for the numerical simulation of scattering from one-and two-dimensional rough surfaces. Applied Optics. vol. 32. No. 15. 2839-2847. May 20, 1993.
Mahmood et al. Near-Infrared Optical Imaging of Protease Activity for Tumor Detection. 866-870. 1999.
Masters et al. Multiphoton Excitation Fluorescence Microscopy and Spectroscopy of In Vivo Human Skin. Biophysical Journal. vol. 72. 2405-2412. Jun. 1997.

(56) References Cited

OTHER PUBLICATIONS

Moats et al. "Smart" Magnetic Resonance Imaging Agent that Report on-Specific Enzymatic Activity. 726-728. 1997.

Mohajerani et al. FMT-PCCT: Hybrid Fluorescence Molecular Tomography—X-Ray Phase-Contrast CT Imaging of Mouse Models. Transactions on Medical Imaging. vol. 33. No. 7. 1434-1446. Jul. 2014.

Neri et al. Targeting by affinity-matured recombinant antibody fragments of an angiogenesis associated fibronectin isoform. Nature Biotechnology. vol. 15. 1271-1276. Sep. 21, 1997.

Ntziachristos, Vasilis. Fluorescence Molecular Imaging. Annu. Rev. Biomed. Eng. vol. 8. 1-33. 2006.

Jun. 28, 2023 (CA) Office Action Application No. 3,095,410.

Sep. 21, 2023 (EP) Examination Report Application No. 18912501.6.

Optical Coherence Tomography with NIR/SWIR, Dec. 9, 2017, pp. 1-5, XP093081730, Retrieved from the Internet: URL: https://web.archive.org/web/20171209053425/http:l/ www.sensorsinc.com/applications/medical/optical-coherencetomography/.

Drexler Wolfgang: "OCT imaging leaps to the next generation", Jan. 1, 2008 (Jan. 1, 2008), pp. 1-8, XP093081773, Retrieved from the Internet: URL: https://www.smithmillermoore.com/Pdfs/technicalarticles/OCT-imaging-leaps-to-the-next-generation.pdf.

\* cited by examiner

SYSTEMS AND METHODS FOR 3D RECONSTRUCTION OF ANATOMICAL ORGANS AND INCLUSIONS USING SHORT-WAVE INFRARED (SWIR) PROJECTION TOMOGRAPHY

RELATED APPLICATION DATA

This application is a National Stage Application under 35 U.S.C. 371 of co-pending PCT application number PCT/US2018/025393 designating the United States and filed Mar. 30, 2018; which is incorporated herein by reference in its entirety.

FIELD OF THE INVENTION

This invention relates generally to methods and systems for tomographic imaging. More specifically, in certain embodiments, this invention relates to tomographic imaging using short-wave infrared (SWIR) radiation.

BACKGROUND OF THE INVENTION

In vivo imaging of small mammals is performed by a large community of investigators in various fields, e.g., oncology, infectious disease, and drug discovery. There is a wide array of technologies directed to in vivo imaging of mammals—for example, bioluminescence, fluorescence, tomography, and multimodal imaging technologies.

Many imaging modalities are tomographic approaches. Tomography is based on detection of light transmitted through or emanating from a sample to obtain images or infer the optical properties of the sample under study. For example, tomographic imaging can be used to reconstruct a map of tissue absorption within a region of interest of a subject under study. In other applications, tomographic imaging is used to generate a map of the spatial distribution of a probe, such as a fluorescent emitter, that is present in the region of interest. Tomographic imaging thus allows construction of detailed images of internal structures of objects, and distribution of a probe within a region of interest of a subject, in a non-invasive fashion.

Optical tomographic imaging can provide valuable information, relevant to analysis of biological processes within a subject under study, that cannot be obtained from non-optical imaging techniques such as micro-CT or magnetic resonance imaging (MRI). For example, maps of tissue absorption at optical wavelengths are capable of providing biological functional information related to hemoglobin concentration and tissue oxygenation state, which can be used to detect certain types of tumors. In addition, optical absorption additionally provides improved contrast for localizing certain organs, such as the heart, in comparison with X-ray imaging or MRI techniques.

Optical tomography can also be used to map the spatial distribution of an administered or endogenous light emitting probe, such as a fluorescent or bioluminescent probe. For example, fluorescent probes absorb light propagating inside of an object and emit light at a longer wavelength (lower energy) than the absorbed light inside of the object, allowing non-invasive, in vivo investigation of functional and molecular signatures in whole tissues of animals and humans. Fluorescence optical tomography systems thereby provide for molecular imaging, which can be used to visually indicate molecular abnormalities that are the basis of a disease, rather than just imaging the anatomical structures in the area of suspected molecular abnormalities, as with conventional imaging approaches. Specific imaging of molecular targets provides earlier detection and characterization of a disease, as well as earlier and direct molecular assessment of treatment efficacy. An illustrative fluorescence optical tomography system is described in U.S. Patent Application Publication No. US2004/0015062, the text of which is incorporated by reference herein, in its entirety.

Current optical techniques for providing tomographic reconstructions of optical absorption within a region of a subject, however, are limited as a result of the strong scattering that light propagating through tissue undergoes. Light scattering limits resolution in and of itself, and also adds complexity to the tomographic reconstruction process by requiring that photon diffusion effects be accurately accounted for. Accounting for photon diffusion in tomographic reconstruction process can cause significant inaccuracies and artifacts via modelling errors and noise.

Moreover, optical tomographic imaging techniques that are used for visualizing administered or endogenous probes within a subject often rely upon a complex tomographic reconstruction process in order to obtain images of a spatial distribution of the probe within the subject. The tomographic reconstruction processing employed in such optical tomographic imaging techniques typically utilizes complex forward models that describe photon propagation in diffusive media in order to infer (e.g. via solution of an inverse problem) the spatial distribution of a given probe using a series of measurements of light emanating from the probe within the region of the subject. Such forward models must account for absorption and multiple scattering of photons within tissue. Accordingly, the accuracy of a forward model, and, in turn, tomographic reconstructions that rely upon the forward model, are limited by the accuracy with which optical properties of the tissue under study are known.

There is a need for systems and methods that provide for accurate and quantitative tomographic imaging of a region of interest in a subject under study, which account for heterogeneous optical properties.

SUMMARY OF THE INVENTION

Presented herein are systems and methods for tomographic imaging of a region of interest in a subject using short-wave infrared (SWIR) light in order to provide for accurate reconstruction of absorption maps within the region of interest. The reconstructed absorption maps are representations of the spatial variation in tissue absorption within the region of interest. The reconstructed absorption maps can themselves be used to analyze anatomical properties and biological processes within the region of interest, and/or be used as input information about anatomical properties in order to facilitate data processing used to obtain images of the region of interest via other imaging modalities. For example, the reconstructed absorption maps may be incorporated into forward models that are used in tomographic reconstruction processing in fluorescence and other contrast-based tomographic imaging modalities. Incorporating reconstructed absorption maps into other tomographic reconstruction processing algorithms in this manner improves the accuracy of the resultant reconstructions.

In certain embodiments, the tomographic imaging approach described herein leverages multi-angle projection tomography, wherein a region of interest of a subject is illuminated with SWIR radiation (e.g. having a wavelength from 1000 nm to 1500 nm, e.g. having a wavelength of 1064 nm) at a plurality of different illumination angles, and for each angle, light passing through the region of interest is detected. In particular, in certain embodiments, transillumination images are collected for each of the illumination angles, wherein the transilluminating light passes from an illumination source, through the region of interest, and to a detector (e.g. an imaging detector such as a focal plane array (e.g. CCD, e.g. CMOS camera) comprising a plurality of pixels) in substantially a straight line. In this manner, a plurality of angular projection measurements are obtained.

In certain embodiments, the obtained angular projection measurements are processed in order to determine a representation corresponding to a tomographic reconstruction of an optical absorption map of the region of interest. As described above, the determined optical absorption map can be used to analyze anatomical properties and biological processes in the region of interest, or as an input into other tomographic reconstruction processing steps used in other imaging modalities.

The SWIR tomographic imaging approach described herein offers advantages over existing optical and non-optical imaging technologies. In particular, existing diffuse optical tomographic imaging techniques rely on non-linear diffuse tomographic reconstruction. The non-linear diffuse tomographic reconstruction process relies on solution of an ill-posed inverse problem, and, as a result, suffers inaccuracies and artifacts are introduced by modelling errors and noise.

Diffuse optical tomography techniques use radiation having a wavelengths in visible (i.e. from 400 to 700 nm) and near-infrared (i.e. from 700 to 900 nm) spectral windows. At such wavelengths, biological tissue is highly scattering, and photons used for imaging undergo strong diffusion. The scattering and diffusion of photons used in diffuse tomographic imaging techniques limits the accuracy and resolution of tomographic images that can be obtained. Moreover, in order to accurately account for photon diffusion in the tomographic reconstruction process used in diffuse optical tomographic, diffusive and complex models (e.g. forward models) are required. The performance of the tomographic reconstruction process is highly dependent upon the proper optimization and parameterization of these models.

In contrast, embodiments of the SWIR tomographic imaging approach described herein utilize radiation in the SWIR spectral window [(e.g. having wavelengths from 1000 nm to 1500 nm), e.g. having a wavelength of 1064 nm)]. The selection of the particular SWIR spectral window, and the implications of its use in tomographic imaging are non-trivial. In particular, the particular SWIR spectral window described herein provides for sufficiently low scattering and absorption of light within tissue. At shorter wavelengths (e.g. wavelengths below 1000 nm), scattering of light by tissue increases, thereby limiting the accuracy and spatial resolution of the tomographic reconstruction that can be obtained. At higher wavelengths (e.g. wavelengths above 1500 nm), absorption is too high for photons to penetrate tissue.

Notably, the use of SWIR radiation does not merely allow for existing diffuse optical tomography approaches to be employed with increased accuracy, but rather allows for the use of a different approach to tomographic reconstruction. In particular, the reduced scattering of SWIR radiation obviates the need to use complex diffusive models of photon transport in the tomographic reconstruction process, and eliminates the need to solve an ill-posed inverse problem in order to obtain a tomographic reconstruction. Instead, the SWIR imaging approach described herein uses a multi-angle projection tomography approach. This approach directly relates the attenuation experienced by a beam of light passing through the region of interest of the subject to the optical properties (e.g. absorption) of the region (e.g. via a Beer's law relation, e.g. via a Radon Transform) and allows for more accurate and quantitative reconstruction.

For example, in certain embodiments, calibration data is used in the tomographic reconstruction in order to provide for absolute quantification of optical absorption in tissue within the region of interest. In certain embodiments, calibration data such as radiation source power, radiometric configuration of the system, and detector intensity response can be used to calibrate detector read outs such that they represent power loss along the optical path of a light beam passing through the sample. Optical absorption maps determined via tomographic reconstructions from such calibrated data are quantitative in nature, each voxel of the optical absorption map providing an absolute quantitative measurement of optical absorption (e.g. in inverse mm or inverse cm) in an associated location in the region of the subject.

In certain embodiments, use of the absorption maps obtained via the SWIR imaging approach described herein in other (e.g. fluorescence, e.g. other contrast-based imaging modalities) tomographic reconstruction procedures offers improvement over the use of absorption maps obtained via non-optical imaging modalities such as micro-CT or magnetic resonance imaging. For example, non-optical imaging modalities do not directly measure (or reconstruct) optical properties of a sample. Instead, non-optical imaging techniques such as MRI aid in establishing an anatomical map of the organs. To map optical properties, such as optical absorption, look-up table approaches must be used to assign predefined absorption coefficients to organs. These approaches suffer from the assumption that organ absorption values and profiles do not change from animal to animal. Moreover, the assumption that organ boundaries are truly representative of the absorptive region boundaries in optical imaging is built into these approaches.

In contrast, the SWIR tomographic imaging approach described herein directly reconstructs a map of optical absorption throughout the region of interest, and does not suffer from any of these limitations.

Accordingly, in providing for accurate and, in certain embodiments, quantitative maps of optical absorption within a region of interest of a subject, the systems and methods described herein facilitate analysis of anatomical properties and biological processes in a subject.

In certain embodiments, the optical absorption maps obtained via the SWIR imaging approach described herein may be used to localize anatomical organs, including the heart and lungs. In certain embodiments, three-dimensional images illustrating the location of one or more anatomical features of a subject are constructed. In certain embodiments, biological inclusions (e.g., tumors or other inclusions with dense and/or leaky vasculatures) are imaged using the methods and systems described herein.

In certain embodiments, the optical data (e.g., optical absorption maps and/or absorption coefficients) obtained via the systems and methods described herein may be utilized to improve the performance of other imaging modalities, such as fluorescence tomography.

For example, optical absorption maps determined via the SWIR tomographic imaging approach described herein can be incorporated as inputs in tomographic reconstructions used in fluorescence tomographic imaging and/or other contrast-based three dimensional imaging modalities (e.g., bioluminescent imaging). These optical absorption maps directly correspond to measurements of heterogeneous optical properties (e.g. optical absorption) in a region of interest of the same subject that is imaged in the fluorescence (or other contrast-based) imaging modality. Such subject-specific optical absorption maps are used in establishing a forward model that accounts for heterogeneous optical properties in a region of interest of the subject for fluorescence tomography reconstructions. The use of subject-specific absorption data obtained directly via SWIR projection tomography of the sample increases the accuracy of the forward model when compared to other methods that rely on predefined absorption coefficients.

Accordingly, by providing an approach for obtaining accurate and/or quantitative maps of optical absorption in a region of a subject, the SWIR tomographic imaging approach described herein provides an advantageous new modality for in vivo imaging. The optical absorption maps that the imaging approach of the systems and methods described herein provide can be used to localize anatomical regions and organs that suffer from reduced contrast in other imaging modalities. Furthermore, the optical absorption maps can be incorporated into other imaging modalities, thereby improving the accuracy of other imaging techniques.

In one aspect, the invention is directed to a method of creating an optical tomographic image of a region of interest of a subject, the method comprising: (a) directing illumination radiation (e.g. short wave infrared light; e.g. infrared light having a wavelength from 1000 nm to 1500 nm) (e.g., from a first source or a first set of sources) into the region of interest of the subject at a plurality of illumination angles, thereby illuminating (e.g., transilluminating) the region of interest (e.g., sequentially illuminating the region of interest at each of the plurality of illumination angles); (b) for each of the plurality of illumination angles, detecting (e.g., sequentially detecting) (e.g., by a first detector or a first set of detectors) (e.g. imaging, e.g. imaging using a focal plane array detector comprising a plurality of pixels) radiation transmitted through the region of interest at a corresponding detection angle [e.g. wherein, for each of the plurality of illumination angles, the transilluminating light passes from the source through the region of interest to the detector in a substantially straight line], thereby obtaining a plurality of angular projection measurements; (c) determining, by a processor of a computing device, a representation corresponding to a tomographic reconstruction of an optical absorption map of the region of interest using data corresponding to the obtained plurality of angular projection measurements.

In certain embodiments, step (a) comprises directing illumination radiation from a first source and step (b) comprises detecting radiation transmitted through the region of interest at a first detector, the first source and the first detector are mounted on a rotating gantry operable to rotate about the subject, and wherein the method comprises, for each of a plurality of positions of the rotating gantry, illuminating the region of interest of the subject at a given illumination angle and detecting radiation transmitted through the region of interest at the corresponding detection angle, thereby obtaining the plurality of angular projection measurements.

In certain embodiments, step (a) comprises directing illumination radiation from a first source and step (b) comprises detecting radiation transmitted through the region of interest at a first detector, the subject is mounted on a rotating table operable to rotate about an axis passing through its center, the first source and first detector are mounted in a fixed position about the subject, and the method comprises, for each of a plurality of positions of the rotating table, illuminating the region of interest of the subject at a given illumination angle and detecting radiation transmitted through the region of interest at the corresponding detection angle, thereby obtaining the plurality of angular projection measurements.

In certain embodiments, step (c) comprises inverting a projection model of radiation transmission (e.g. wherein the projection model is a Radon Transform of the region of interest, e.g. wherein the projection model is a Beer's Law model of optical absorption in the region of interest) from a first source, through the region of interest of the subject, to a first detector (e.g. the projection model relates the intensity of the detected radiation to the intensity of the illumination radiation as a function of positional variation in optical absorption coefficients within the region of interest) at each of the plurality of illumination angles and corresponding detection angles.

In certain embodiments, inverting the projection model comprises applying an inverse operator of the projection model (e.g. an inverse Radon Transform) to a plurality of observation values determined using the data corresponding to the plurality of angular projection measurements [e.g. wherein the plurality of observation values are the data corresponding to the plurality of angular projection measurements; e.g. the observation values correspond to attenuation values determined from the data corresponding to the plurality of angular projection measurements (e.g. determined by taking a logarithm of the ratio of (i) a signal corresponding to a power of the detected radiation to (ii) a signal corresponding to a power of the illumination radiation)], thereby determining the optical absorption map of the region of interest (e.g. application of the inverse operator to the observation values based on data corresponding to the plurality of angular projection measurements yields a function describing positional variation in absorption coefficients within the region of interest).

In certain embodiments, the projection model is a discretized model that relates [e.g. via a linear system of equations (e.g. represented in matrix form)], for each of the plurality of angular measurements, (i) a value corresponding to an intensity of the detected radiation at the angular measurement to (ii) a plurality of optical absorption coefficients, each representing optical absorption (e.g. occurring at a wavelength of the illumination source) at a specific point within the region of interest (e.g., (ii) a spatial distribution of optical absorption within the region of interest).

In certain embodiments, the method comprises applying a discretized version of the inverse operator of the projection model, wherein the discretized inverse operator of the projection model relates, for each of a plurality of discretized locations (e.g. voxels or pixels) representing physical locations (e.g., 3D or 2D) in the region of interest, a value of an optical absorption coefficient at the location to at least a portion of the plurality of observation values determined using the data corresponding to the angular projection measurements, thereby determining, for each of the plurality of discretized locations, a corresponding value of the optical absorption coefficient, thereby determining the optical absorption map of the region of interest.

In certain embodiments, step (c) comprises determining the optical absorption map of the region of interest using the data corresponding to the plurality of angular projection measurements and calibration data in order to determine the optical absorption map of the region of interest, wherein the optical absorption map is quantitative (e.g. by using calibration data in conjunction with the angular projection measurements to convert data corresponding to detected radiation to a quantitative representation of power loss along an optical path from a first source to a first detector).

In certain embodiments, the calibration data comprises at least one member selected from the group consisting of: data corresponding to a power of the source; data corresponding to measurement(s) of a radiometric configuration of the system; and data corresponding to an intensity response of the detector (e.g. a measured responsivity, e.g. a measured responsivity for each of a plurality of pixels that the detector comprises).

In certain embodiments, the method comprises obtaining a measurement of one or more boundaries representing a surface of the subject about the region of interest (e.g., using surface scanning or X-ray microCT), wherein step (c) comprises determining the optical absorption map of the region of interest using the measurement of the one or more boundaries (e.g. by limiting a reconstruction space corresponding to the region of interest to a volume contained within the one or more measured boundaries).

In certain embodiments, the method comprises applying one or more denoising filters (e.g., Bilateral filters) to the data corresponding to the plurality of angular projection measurements.

In certain embodiments, the optical absorption map is a three dimensional (3-D) map.

In certain embodiments, the region of interest comprises one or more anatomical organs (e.g. a heart, e.g. lungs of the subject) and the method comprises processing the optical absorption map to automatically localize (e.g. identify, e.g. identify contours of) the one or more anatomical organs in the optical absorption map.

In certain embodiments, the method comprises: recording at each of a plurality of time points, a corresponding set of a plurality of angular projection measurements; and for each of the plurality of time points, determining, by the processor, a corresponding optical absorption map of the region of interest using data corresponding to the corresponding set of the plurality of angular projection measurements, thereby determining a plurality of optical absorption maps representing optical absorption in the region of interest at each of the plurality of different time points.

In certain embodiments, a temporal separation between each of the plurality of time points is sufficiently small so as to provide video rate images of optical absorption in the region of the subject.

In certain embodiments, the method comprises using the determined optical absorption map to obtain a tomographic representation of a distribution of a fluorescent and/or bioluminescent emitter (e.g. species, e.g. probes) within the region of the subject.

In certain embodiments, the method comprises: (d) illuminating, by an excitation source (e.g. the same source as the first source; e.g. a different source from the first source), the region of interest with excitation light, the excitation light having a wavelength corresponding to an excitation wavelength of a fluorescent emitter present in the region of interest; (e) detecting, by a fluorescence detector (e.g. the same detector as the first detector; e.g. a different detector from the first detector), fluorescent light emitted from the plurality of fluorescent emitters in the region of interest, the fluorescence detector responsive to light having a wavelength corresponding to an emission wavelength of the fluorescent emitter present in the region of interest; and (f) determining, by the processor, a tomographic representation of the distribution of the fluorescent emitter in the region of interest using data corresponding to the detected fluorescent light and the determined optical absorption map.

In certain embodiments, step (d) comprises illuminating the region of interest with excitation light using a plurality of different excitation source positions.

In certain embodiments, step (e) comprises detecting emitted fluorescent light using at a plurality of different fluorescent detector positions.

In certain embodiments, step (e) comprises inverting a forward model that describes (i) excitation light propagation from a point corresponding to an excitation source position to a point corresponding to a position of a fluorescent emitter in the region of interest and (ii) emission light propagation from the position of the fluorescent emitter to a point corresponding to a fluorescence detector position.

In certain embodiments, the method comprises using the determined optical absorption map in the forward model.

In certain embodiments, the method comprises determining, by the processor, a map of the quantity (e.g., concentration) of the fluorescent emitter in the region of interest using data corresponding to the detected fluorescent light and the determined optical absorption map.

In another aspect, the invention is directed to a system for creating an optical tomographic image of a region of interest of a subject, the system comprising: (a) a sample stage for mounting a subject (e.g. in a fixed position during imaging); (b) a first source aligned to direct illumination radiation into the region of interest of the subject; (c) a first detector aligned to detect radiation from the first source, transmitted through the region of interest of the subject; (d) a memory for storing a set of instructions; and (e) a processor for executing the instructions, wherein: the sample stage, first source, and first detector are positioned to allow illumination of the region of interest at a plurality of illumination angles and to allow detection of radiation transmitted through the region of interest at a plurality of corresponding detection angles to obtain a plurality of angular projection measurements, and the instructions, when executed by the processor cause the processor to determine a representation corresponding to a tomographic reconstruction of an optical absorption map of the region of interest using data corresponding to the plurality of angular projection measurements.

In certain embodiments, the first source and the first detector are mounted on a rotating gantry operable to rotate about the subject [e.g., such that each of the plurality of angular projection measurements corresponds to a rotational position of the rotating gantry (e.g., each rotational position of the rotating gantry corresponding to a particular illumination and detection angle)].

In certain embodiments, the subject is mounted on a rotating table operable to rotate about an axis passing through its center, and the first source and first detector are mounted in a fixed position about the subject [e.g., such that each of the plurality of angular projection measurements corresponds to a rotational position of the rotating table on which the subject is mounted (e.g., each rotational position corresponding to a particular illumination and detection angle)].

In certain embodiments, the instructions cause the processor to determine the optical absorption map by inverting a projection model of radiation transmission (e.g. wherein the projection model is a Radon Transform of the region of interest, e.g. wherein the projection model is a Beer's Law model of optical absorption in the region of interest) from the first source, through the region of interest of the subject, to the first detector (e.g. the projection model relates the intensity of the detected radiation to the intensity of the illumination radiation as a function of positional variation in optical absorption coefficients within the region of interest) at each of the plurality of illumination angles and corresponding detection angles.

In certain embodiments, inverting the projection model comprises applying an inverse operator of the projection model (e.g. an inverse Radon Transform) to a plurality of observation values determined using the data corresponding to the plurality of angular projection measurements [e.g. wherein the plurality of observation values are the data corresponding to the plurality of angular projection measurements; e.g. the observation values correspond to attenuation values determined from the data corresponding to the plurality of angular projection measurements (e.g. determined by taking a logarithm of the ratio of (i) a signal corresponding to a power of the detected radiation to (ii) a signal corresponding to a power of the illumination radiation)], thereby determining the optical absorption map of the region of interest (e.g. application of the inverse operator to the observation values based on data corresponding to the plurality of angular projection measurements yields a function describing positional variation in absorption coefficients within the region of interest).

In certain embodiments, the projection model is a discretized model that relates [e.g. via a linear system of equations (e.g. represented in matrix form)], for each of the plurality of angular measurements, (i) a value corresponding to an intensity of the detected radiation at the angular measurement to (ii) a plurality of optical absorption coefficients, each representing optical absorption (e.g. occurring at a wavelength of the illumination source) at a specific point within the region of interest (e.g., (ii) a spatial distribution of optical absorption within the region of interest).

In certain embodiments, the instructions cause the processor to determine the optical absorption map by applying a discretized version of the inverse operator of the projection model to determine, for each of the plurality of discretized locations, a corresponding value of the optical absorption coefficient, wherein the discretized inverse operator of the projection model relates, for each of a plurality of discretized locations (e.g. voxels or pixels) representing physical locations (e.g., 3D or 2D) in the region of interest, a value of an optical absorption coefficient at the location to at least a portion of the plurality of observation values determined using the data corresponding to the angular projection measurements.

In certain embodiments, the instructions cause the processor to determine the optical absorption map using the data corresponding to the plurality of angular projection measurements and calibration data, wherein the optical absorption map is quantitative (e.g. wherein the instructions cause the processor to determine the tomographic reconstruction of the optical absorption map by using calibration data in conjunction with the angular projection measurements to convert data corresponding to detected radiation to a quantitative representation of power loss along an optical path from the first source to the first detector).

In certain embodiments, the calibration data comprises at least one member selected from the group consisting of: data corresponding to a power of the source; data corresponding to measurement(s) of a radiometric configuration of the system; and data corresponding to an intensity response of the detector (e.g. a measured responsivity, e.g. a measured responsivity for each of a plurality of pixels that the detector comprises).

In certain embodiments, the system comprises a surface scanning module for obtaining a measurement of one or more boundaries representing a surface of the subject about the region of interest (e.g., using surface scanning or X-ray microCT measurements), wherein the instructions cause the processor to determine the optical absorption map using the measurement of the one or more boundaries (e.g. by limiting a reconstruction space corresponding to the region of interest to a volume contained within the one or more measured boundaries).

In certain embodiments, the instructions cause the processor to apply one or more denoising filters (e.g., Bilateral filters) to the data corresponding to the plurality of angular projection measurements.

In certain embodiments, the optical absorption map is a three dimensional (3-D) map.

In certain embodiments, the region of interest comprises one or more anatomical organs (e.g. a heart, e.g. lungs of the subject) and the instructions cause the processor to process the optical absorption map to automatically localize (e.g. identify, e.g. identify contours of) the one or more anatomical organs in the optical absorption map.

In certain embodiments, the sample stage, first source, and first detector are operable (e.g., in combination) to allow recording at each of a plurality of time points, a corresponding set of a plurality of angular projection measurements, and wherein the instructions cause the processor to: for each of the plurality of time points, determine a corresponding optical absorption map of the region of interest using data corresponding to the corresponding set of the plurality of angular projection measurements, thereby determining a plurality of optical absorption maps representing optical absorption in the region of interest at each of the plurality of different time points.

In certain embodiments, a temporal separation between each of the plurality of time points is sufficiently small so as to provide video rate images of optical absorption in the region of the subject.

In certain embodiments, the instructions cause the processor to use the determined optical absorption map to obtain a tomographic representation of a distribution of a fluorescent and/or bioluminescent emitter (e.g. species, e.g. probes) within the region of the subject.

In certain embodiments, the system comprises: (d) an excitation source (e.g. the same source as the first source; e.g. a different source from the first source) aligned to direct excitation light into the region of interest of the subject, the excitation light having a wavelength corresponding to an excitation wavelength of a fluorescent emitter present in the region of interest; and (e) a fluorescence detector (e.g. the same detector as the first detector; e.g. a different detector from the first detector), aligned to detect fluorescent light emitted from the plurality of fluorescent emitters in the region of interest, wherein the fluorescence detector responsive to light having a wavelength corresponding to an emission wavelength of the fluorescent emitter present in the region of interest, wherein the instructions cause the processor to determine a tomographic representation of the distribution of the fluorescent emitter in the region of interest using data corresponding to the detected fluorescent light and the determined optical absorption map.

In certain embodiments, the excitation source is operable direct the excitation into the region of interest from a plurality of different excitation source positions.

In certain embodiments, the fluorescence detector is operable to detect fluorescent light emitted from the region of interest at a plurality of different fluorescent detector positions.

In certain embodiments, the instructions cause the processor to determine the tomographic representation of the distribution of the fluorescent emitter by inverting a forward model that describes (i) excitation light propagation from a point corresponding to an excitation source position to a point corresponding to a position of a fluorescent emitter in the region of interest and (ii) emission light propagation from the position of the fluorescent emitter to a point corresponding to a fluorescence detector position.

In certain embodiments, the instructions cause the processor to use the determined optical absorption map in the forward model.

In certain embodiments, the instructions cause the processor to determine a map of the quantity (e.g., concentration) of the fluorescent emitter in the region of interest using data corresponding to the detected fluorescent light and the determined optical absorption map.

BRIEF DESCRIPTION OF THE FIGURES

The foregoing and other objects, aspects, features, and advantages of the present disclosure will become more apparent and better understood by referring to the following description taken in conjunction with the accompanying drawings, in which.

DEFINITIONS

Figure 1:
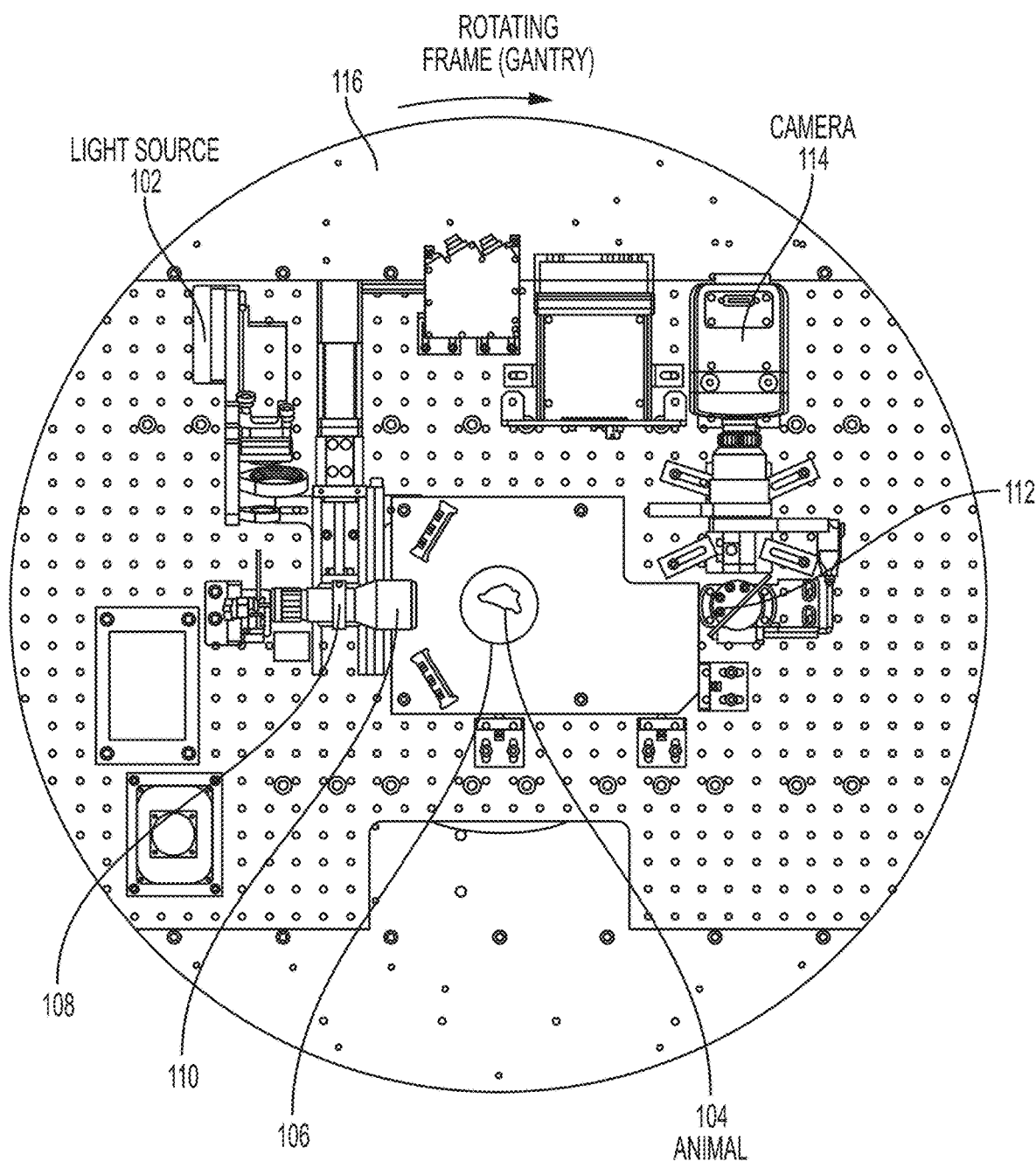
FIG. 1 is a schematic of a system for in vivo transmission imaging, according to an illustrative embodiment of the invention.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context and except where such number would exceed 100% of a possible value.

Image: As used herein, an "image"—for example, a 3-D image of mammal—includes any visual representation, such as a photo, a video frame, streaming video, as well as any electronic, digital or mathematical analogue of a photo, video frame, or streaming video. Any apparatus described herein, in certain embodiments, includes a display for displaying an image or any other result produced by the processor. Any method described herein, in certain embodiments, includes a step of displaying an image or any other result produced via the method.

3-D, three-dimensional: As used herein, "3-D" or "three-dimensional" with reference to an "image" means conveying information about three dimensions. A 3-D image may be rendered as a dataset in three dimensions and/or may be displayed as a set of two-dimensional representations, or as a three-dimensional representation. In certain embodiments, a 3-D image is represented as voxel (e.g., volumetric pixel) data.

Map: As used herein, the term "map" is understood to mean a visual display, or any data representation that may be interpreted for visual display, which contains spatially-correlated information. For example, a three-dimensional map of a given volume may include a dataset of values of a given quantity that varies in three spatial dimensions throughout the volume. A three-dimensional map may be displayed in two-dimensions (e.g., on a two-dimensional screen, or on a two-dimensional printout).

Fluorescence image, emission image: As used herein, the terms "fluorescence image" or "emission image" are understood to mean an image acquired at a wavelength corresponding to an emission wavelength of a fluorescent agent or probe.

Electromagnetic radiation, radiation: As used herein, the term "electromagnetic radiation" or "radiation" is understood to mean self-propagating waves in space of electric and magnetic components that oscillate at right angles to each other and to the direction of propagation, and are in phase with each other. Electromagnetic radiation includes: radio waves, microwaves, red, infrared, and near-infrared light, visible light, ultraviolet light, X-rays and gamma rays.

Short-wave infrared, SWIR: As used herein, the term "short-wave infrared (SWIR) light" is understood to mean any radiation comprising electromagnetic radiation with a wavelength between 1000 nm-1500 nm.

Detector: As used herein the term "detector" includes any detector of electromagnetic radiation including, but not limited to, CCD camera, photomultiplier tubes, photodiodes, and avalanche photodiodes.

Forward model: As used herein, the term "forward model" is understood to mean a physical model of light propagation (e.g., photon transport) in a given medium from a source to a detector.

DETAILED DESCRIPTION

It is contemplated that systems, devices, methods, and processes of the claimed invention encompass variations and adaptations developed using information from the embodiments described herein. Adaptation and/or modification of the systems, devices, methods, and processes described herein may be performed, as contemplated by this description.

Throughout the description, where articles, devices, and systems are described as having, including, or comprising specific components, or where processes and methods are described as having, including, or comprising specific steps, it is contemplated that, additionally, there are articles, devices, and systems of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

Documents are incorporated herein by reference as noted. Where there is any discrepancy in the meaning of a particular term, the meaning provided in the Definition section above is controlling.

Headers are used herein to aid the reader and are not meant to limit the interpretation of the subject matter described.

Described herein are systems and methods for tomographic imaging of a region of interest of a subject using short-wave infrared (SWIR) optical radiation (e.g. comprising optical radiation having a wavelength between 1000 nm and 1500 nm). In certain embodiments, the SWIR tomographic imaging approach described herein provides for reconstruction of optical absorption maps that represent spatially varying optical absorption within a region of interest of a subject (e.g. an animal, e.g. a small mammal). In certain embodiments, the region of interest comprises substantially the whole body of the subject, such that the approach provides for whole body imaging of a subject.

In certain embodiments, the optical absorption maps are three-dimensional maps. In certain embodiments, the optical absorption maps are quantitative optical absorption maps that provide absolute quantification of optical absorption throughout a region of interest of a subject.

In certain embodiments, the optical absorption maps are used to establish a forward model for fluorescence tomographic imaging. Establishing a forward model by use of subject-specific absorption data obtained directly by SWIR projection tomography of the sample of interest can provide for increased accuracy of forward models in comparison with other methods that rely on predefined absorption coefficients. The accuracy of a forward model used in a tomographic reconstruction algorithm in turn affects the accuracy of the tomographic reconstruction procedure. Accordingly, by allowing for subject-specific absorption maps to be obtained and used in creating forward models for use in tomographic reconstruction procedures, the approaches described herein improve the accuracy of tomographic imaging procedures, such as fluorescence tomographic imaging.

A. Multi-Angle Projection Tomography

In certain embodiments, the systems and methods described herein provide for multi-angle projection tomography using illumination radiation corresponding to SWIR radiation (e.g., having a wavelength from 1000 nm to 1500 nm) in order to provide a representation corresponding to a tomographic reconstruction of an absorption map of a region of interest of a subject.

In certain embodiments, illumination radiation is directed into the subject at a plurality of illumination angles, thereby illuminating the region of interest. At each of the illumination angles, radiation travels along a substantially straight path (represented by an illumination ray corresponding to a given illumination angle), into the region of interest of the subject. A given illumination angle corresponds to an angle measured, in a given direction of rotation, between the given illumination ray and a fixed reference axis. For example, as used herein, a given illumination angle measured relative to a ventral position of a subject refers to an angle measured between the corresponding illumination ray and an axis passing from a dorsal to a ventral side of the subject, wherein the angle is measured with respect to the ventral side of the subject, in a clockwise direction within a transverse plane.

In certain embodiments, for each of the plurality of illumination angles, radiation transmitted through the region of interest is detected at a corresponding detection angle. Each of measurement of detected radiation transmitted through the region of interest for a given illumination and corresponding detection angle represents an angular projection measurement. Accordingly, by detecting, for each of a plurality of illumination angles, radiation transmitted through the region of interest at a corresponding detection angle, as described, a plurality of angular projection measurements are obtained.

In certain embodiments, for each illumination angle, transilluminating light passing through the region of interest of the subject, from the source to the detector in a substantially straight line is detected. It should be understood that in order to detect transilluminating light, an entire optical path from the source to the detector need not be a straight line, and additional optics before and after the subject (e.g. mirrors, lenses, beam-splitters and the like) may be placed in the optical path and alter a direction travelled by light.

Once the plurality of angular projection measurements has been obtained, a representation corresponding to a tomographic reconstruction of an optical absorption map of the region of interest can be determined using data corresponding to the obtained plurality of angular projection measurements. Further details of the tomographic reconstruction approach for determining the optical absorption map will be described in the following.

B. Systems for Multi-Angle SWIR Projection Tomography

FIG. 1 shows a schematic of an example system for obtaining the plurality of angular projection measurements used in determination of the optical absorption map. The example system provides for in vivo transmission imaging of a region of interest of a subject. In the example system, illumination light from a first source 102 is directed into a region interest of a subject. In certain embodiments, the first source 102, is laser that produces SWIR radiation (e.g., radiation having a wavelength from 1000 nm to 1500 nm; e.g. a fiber laser operating at 1064 nm).

In certain embodiments, the illumination radiation is collimated by a collimator 108 to provide a substantially collimated beam of illumination radiation. The collimated beam is directed to a beam expander 110 to broaden a waist of the beam. In certain embodiments, the waist of the beam is broadened such that the collimated beam fills (e.g. fully illuminates) the region of interest of the subject 104. In some embodiments, a light guide (e.g., a fiber) is used to couple the illumination light from the illumination light source to one or more optical elements (e.g., a collimator 108 or beam expander 110). In certain embodiments, the beam waist is approximately 10 mm In certain embodiments, the illumination light is directed into a region of interest of a subject 104 mounted (e.g. in a fixed position during imaging) on a sample table or stage 106, thereby illuminating the region of interest. A portion of the illumination light propagates through the region of the subject 104.

In the system shown in FIG. 1, a first detector 112 is aligned to detect transilluminating light passing through the region of interest in a substantially straight line. As shown in the figure, in certain embodiments, one or more optical elements (e.g., a mirror) are used to direct the transillumination light having passed through the subject 104 in a substantially straight line to the first detector 114.

In certain embodiments, the first detector is an imaging detector, such as a focal plane array (e.g. a CCD, a CMOS camera) comprising a plurality of light sensitive pixels. Accordingly, in certain embodiments, each angular projection measurement corresponds to a two-dimensional transillumination image of the illumination light passing through the region of interest. In the example system shown in FIG. 1, the first detector 114 is a SWIR-sensitive camera equipped with SWIR optics. In certain embodiments, an enclosure covers the system to prevent interference from external or ambient light sources.

In certain embodiments, the first source, first detector, and sample stage are positioned to allow illumination of the region of interest at a plurality of illumination angles and to allow detection of radiation transmitted through the region of interest at a plurality of corresponding detection angles to obtain a plurality of angular projection measurements.

For example, in certain embodiments each of the plurality of angular projection measurements is obtained in a sequential fashion. In particular, the system directs illumination radiation from the first source, into the sample at a given illumination angle, and detecting transmitted radiation at a corresponding given detection angle (e.g. detecting transilluminating radiation), thereby obtaining an angular projection measurement associated with the given illumination angle. The relative position(s) of the source, detector, and sample stage are then varied in order to vary the illumination angle, and, similarly, a next angular projection measurement associated with the new illumination angle is obtained. This process is repeated until a desired plurality of angular projection measurements are thereby obtained, sequentially.

In certain embodiments, varying the illumination angle is achieved by virtue of a rotating gantry 116 on which the first source and first detector are mounted. The gantry 116 can be rotated, such that the first source 102 and associated optics (e.g. the collimator 108 and beam expander 110) as well as the first detector 114 and any associated optics (e.g. a mirror 112) are rotated about the subject, while the sample stage and subject are maintained in a fixed position. Each of a plurality of positions of the rotating gantry thereby provides a different given illumination angle, allowing for a different associated angular projection measurement to be obtained.

In certain embodiments, the sample stage is operable to rotate (e.g. about an axis passing through its center), and the first source, first detector, and associated optics are maintained in fixed positions about the subject. Rotation of the sample stage thereby provides for variation of the illumination angle. In particular, each of a plurality of rotational positions of the sample stage provides a different given illumination angle, allowing for a different associated angular projection measurement to be obtained.

In certain embodiments, multiple sources and detectors are aligned about the subject and used to provide illumination of the region of interest at the plurality of illumination angles and, for each of the plurality of illumination angles, detection of radiation transmitted through the region of interest at a corresponding detection angle.

Figure 2:
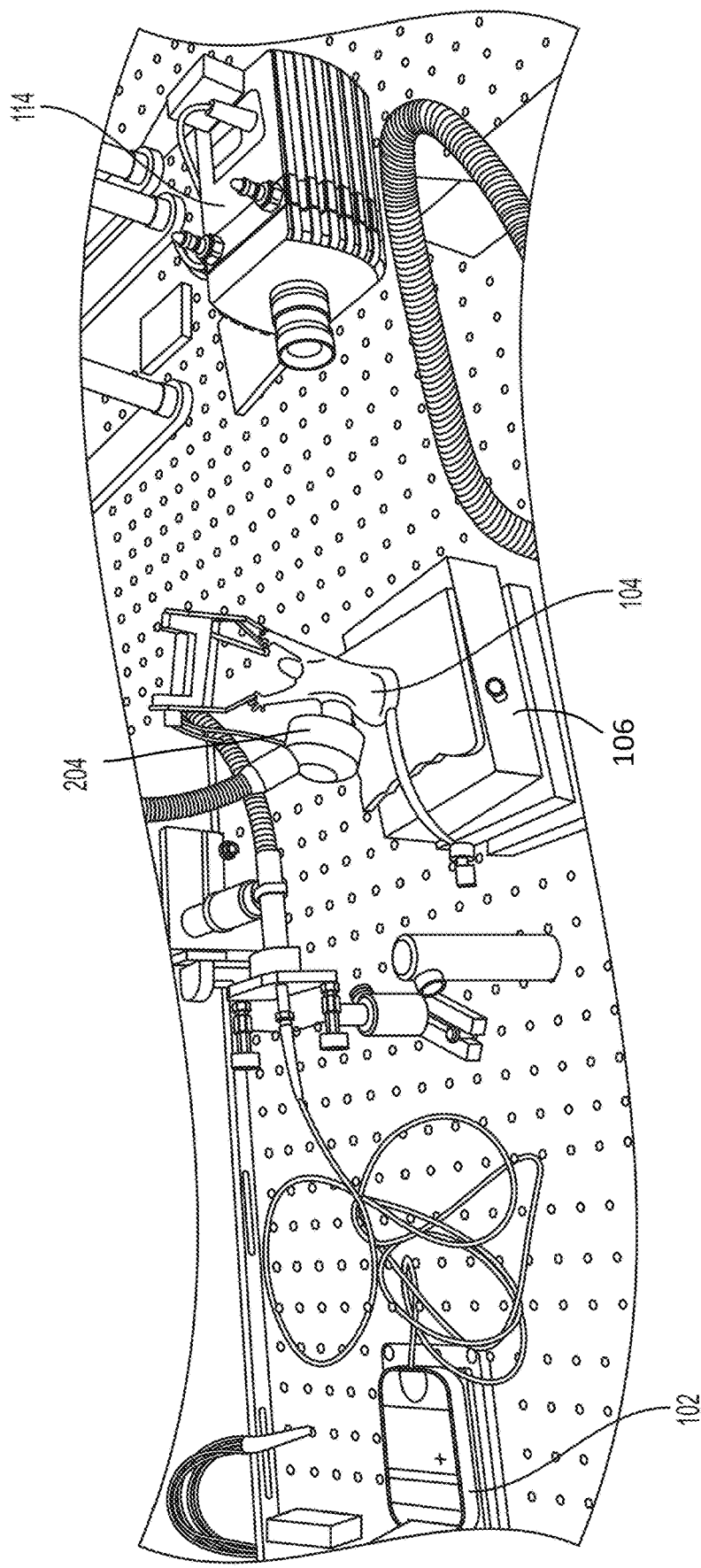
FIG. 2 is an image of a system for in vivo transmission imaging, according to an illustrative embodiment.

FIG. 2 shows an image of a system used for in vivo transmission imaging according to an illustrative embodiment. Light from a 1064 nm fiber laser acting as the illumination light source 102 is collimated and coupled into a light guide 204. The subject 104 is illuminated with a broad cone-type beam from the light guide 204. An InGaAs camera acts as a detector 114 to detect the transillumination light. The subject 104 may be rotated in order to obtain a plurality of transillumination images each corresponding to a different angular projection measurement associated with a given illumination angle.

In certain embodiments, a radiation power level of the illumination light produced by the illumination light source 102 is adjusted. In certain embodiments, the radiation power level of the illumination light is adjusted to ensure a level of radiation to which an animal is exposed is below a maximum permissible radiation exposure level for animal skin. In certain embodiments, a gain and exposure time of a detector 114 is adjusted to ensure each of a plurality of signals, each corresponding to a pixel of a plurality of pixels of the detector are above a noise floor and also below sensor a saturation level associated with the detector. In certain embodiments, the detector 114 operates in an automated light control mode in which said gain and exposure time are automatically and dynamically adjusted.

Figure 3:
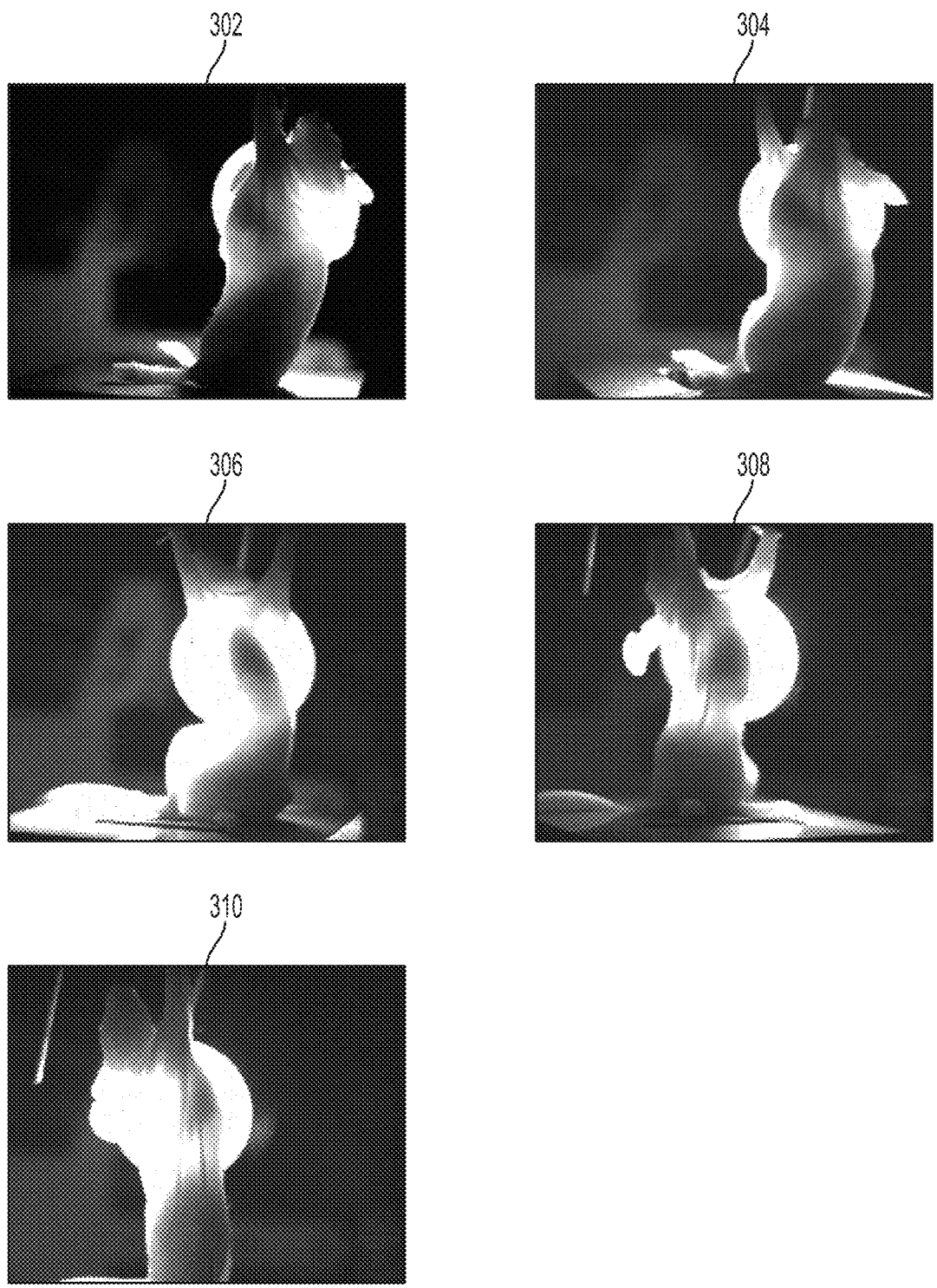
FIG. 3 is a series of transillumination images of a nu/nu mouse thoracic cavity taken at a plurality of illumination angles, according to an illustrative embodiment.

Turning to FIG. 3, a series of transillumination images 302, 304, 306, 308, and 310, each corresponding to an angular projection measurement associated with a different illumination angle are shown. The subject under study is a nu/nu mouse, and an illuminated region of interest corresponds to a thoracic cavity of the mouse. Each of the transillumination images was obtained using illumination radiation having a wavelength of 1064 nm.

Image 302 corresponds to an angular projection measurement associated with an illumination angle of −90 degrees measured relative to a ventral position of the mouse. Image 304 corresponds to an angular projection measurement associated with an illumination angle of −45 degrees measured relative to a ventral position of the mouse. Image 306 corresponds to an angular projection measurement associated with an illumination angle of 0 degrees measured relative to a ventral position of the mouse. Image 308 corresponds to an angular projection measurement associated with an illumination angle of 45 degrees measured relative to a ventral position of the mouse. Image 310 corresponds to an angular projection measurement associated with an illumination angle of 90 degrees measured relative to a ventral position of the mouse.

In each of the series of images, a dark regions represents highly absorptive regions of the thoracic cavity (e.g., corresponding to the heart and lungs) and bright areas correspond to regions and organs characterized by low optical absorption.

Considering the low exposure times required for acquiring transillumination images such as the ones in FIG. 3, in certain embodiments, the approach described herein can also be used towards a host of two dimensional in vivo imaging applications including monitoring heart activity.

B. Reconstruction for Determining Optical Absorption Maps

Figure 4:
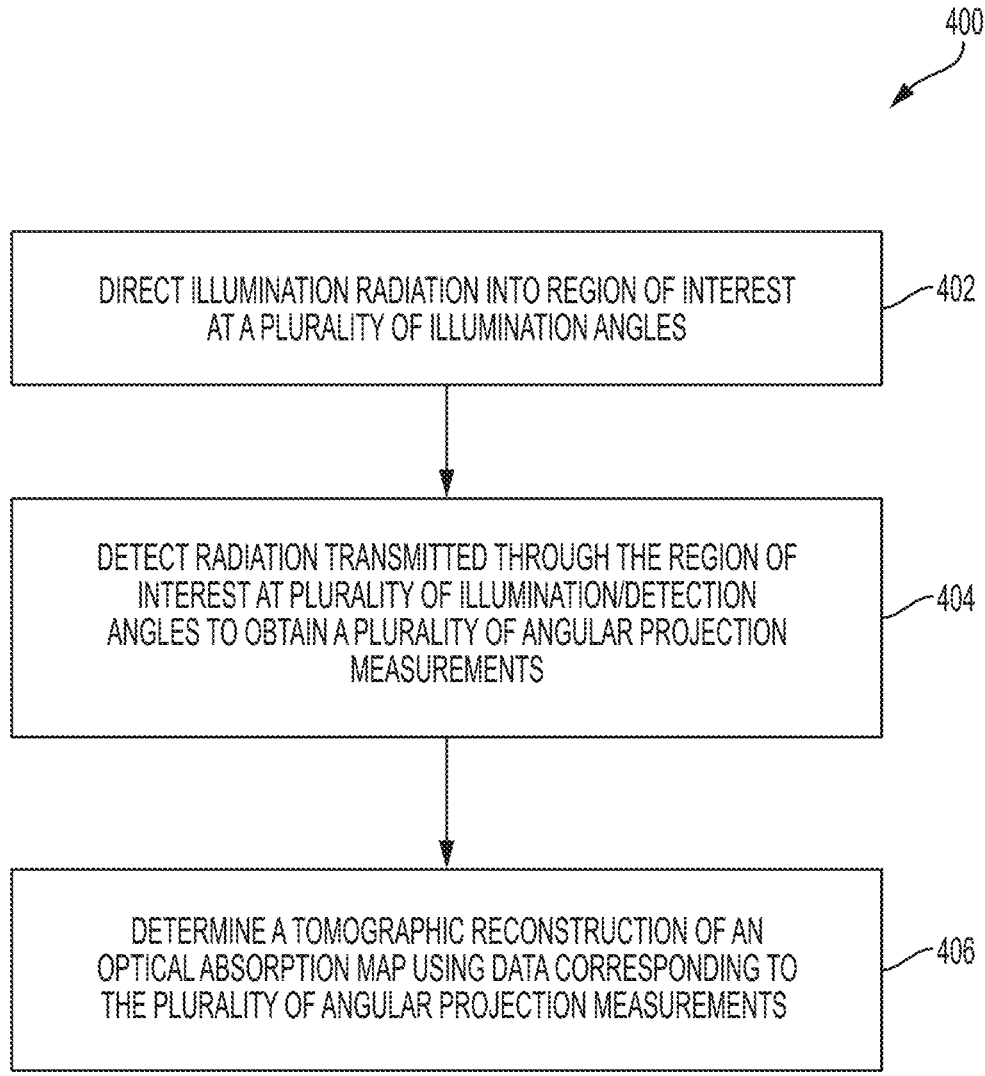
FIG. 4 is a block flow diagram of a process for determining a representation corresponding to a tomographic reconstruction of a three dimensional optical absorption map of a region of interest in a subject, according to an illustrative embodiment.

Angular projection measurements obtained via systems such as those described herein and shown in FIG. 1 and FIG. 2 can be used to determine an optical absorption map of a region of interest of a subject via tomographic reconstruction, for example, via the process 400 shown in FIG. 4. As shown in FIG. 4, illumination radiation is directed into the region of interest 402 at a plurality of illumination angles, and detected at corresponding detection angles to obtain the plurality of angular projection measurements 404. Data corresponding to the plurality of angular projection measurements can then be used to in a tomographic reconstruction procedure to obtain an optical absorption map of the region of interest 406.

The tomographic reconstruction procedure may be based on a projection model of radiation transmission through the region of interest of the subject. Such a projection model may relate, for each of the plurality of illumination angles and corresponding detection angles, a value corresponding to an intensity of detected radiation to an intensity of the illumination radiation as a function of positional variation in optical absorption coefficients within the region of interest. For example, the attenuation of a beam of illumination radiation passing through the region of interest can be expressed in terms of spatially varying optical absorption within the region of interest via a Beer's law relation. In certain embodiments, a Radon transform is used as the projection model. Such projection models may be inverted to determine, from the plurality of angular projection measurements, an optical absorption map representing spatially varying optical absorption within the region of interest.

In certain embodiments, the projection model is established in a discretized form, such that it relates, for each of the plurality of angular projection measurements, (i) a value corresponding to an intensity of the detected radiation at the angular measurement to (ii) a plurality of optical absorption coefficients, each representing optical absorption (e.g. occurring at a wavelength of the illumination source) at a specific discrete location within the region of interest. Accordingly, in certain embodiments, the projection model takes the form of a linear system of equations (e.g. one equation for each of the angular projection measurements; e.g. one equation for each pixel of each transillumination image). The linear system of equations can be written in matrix form, and inversion techniques can be used to solve for the plurality of optical absorption coefficients based on data corresponding to intensities of detected radiation at each angular projection measurement.

In certain embodiments, inversion of the projection model is achieved via application of an inverse operator of the projection model (e.g. an inverse of Beer's law, e.g. an inverse Radon Transform) to observation values determined from the plurality of angular projection measurements. The inverse operator may be applied in discretized form, such that it relates for each of a plurality of discretized locations (e.g. voxels or pixels) representing physical locations (e.g., 3D or 2D) in the region of interest, a value of an optical absorption coefficient at the location to at least a portion of the plurality of observation values determined using the data corresponding to the angular projection measurements. In this manner, absorption coefficient values at one or more physical locations can be determined from observation values of one or more angular projection measurements. An optical absorption map can thus be built up by determining values of absorption coefficients at physical locations throughout the region of interest.

In certain embodiments, the plurality of observation values correspond directly to (e.g. are) the plurality of angular projection measurements. In certain embodiments, the observation values correspond to attenuation values determined from the data corresponding to the plurality of angular projection measurements (e.g. determined by taking a logarithm of the ratio of (i) a signal corresponding to a power of the detected radiation to (ii) a signal corresponding to a power of the illumination radiation).

In certain embodiments, the optical absorption map determined via inversion of the projection model is a three-dimensional map, comprising a plurality of voxels. The values in each voxel represent the level of absorption corresponding to that location in the animal volume. Each voxel of the map is each associated with an optical absorption value and a volume about a particular location within the region of interest. For each voxel, the associated optical absorption value corresponds to a measure of the attenuation experienced by light passing through the volume about the particular location with which the voxel is associated.

The associated optical absorption value may correspond to an average value of optical absorption over the volume about the particular location. In certain embodiments, the optical absorption value is a quantitative absolute measure of optical absorption (e.g. corresponding to a value in inverse length), and the optical absorption map is a quantitative optical absorption map. Quantitative optical absorption maps can be determined using calibration data in conjunction with the obtained angular projection measurements, as will be described in the following. In certain embodiments, the optical absorption value is a relative measure of optical absorption, measured with respect to a known reference (e.g. normalized to an optical absorption value of another voxel in the map).

In certain embodiments, the optical absorption value also accounts for scattering effects (e.g., in addition to absorption) and, accordingly, corresponds to an extinction value or extinction coefficient. Accordingly, in certain embodiments, the optical absorption map is an extinction map (e.g., comprising extinction values that account for absorption and scattering effects).

In certain embodiments, a measurement of one or more boundaries representing a surface of the surface about the region of interest is obtained, for example, through surface scanning or other anatomical imaging techniques (e.g., X-ray microCT). In certain embodiments, the measurement of the one or more boundaries is used in the tomographic reconstruction process in order to determine the optical absorption map of the region of interest. In particular, in certain embodiments, a reconstruction space is limited to a volume contained within the one or more measured boundaries of the subject's surface extracted through existing methodologies.

C. Calibration Data for Quantitative Optical Absorption Maps

In certain embodiments, a quantitative optical absorption map providing absolute quantification of optical absorption within the region of interest of the subject can be obtained by incorporating calibration data into the tomographic reconstruction process used to determine the optical absorption map from the angular projection measurements.

In particular, in certain embodiments, calibration data comprising at least one of a radiation source power, a radiometric configuration of the system, and a detector intensity response is obtained and used along with the angular projection measurements in order to determine the quantitative optical absorption map.

In particular, in certain embodiments, transillumination images are obtained via an imaging detector, and each pixel of the transillumination image representing a value corresponding to a signal (e.g. a voltage, e.g. a current, e.g. a pixel count) produced by a corresponding pixel of the imaging detector in response to radiation that is transmitted through the region of interest of the subject and incident on the detector pixels (e.g. transilluminating radiation incident on the detector pixels). Calibration data corresponding to a detector intensity response is used to convert the signal from each of the plurality of pixels of the detector to a measure of photons per second (e.g. incident on a respective pixel). Calibration data corresponding to the radiation source power and the radiometric properties of the system is used to convert the signal from each of the plurality of pixels of the detector to a quantitative measure of power loss along an optical path of a collimated light beam travelling from the illumination source, through the region of interest, to the detector.

Accordingly, for each value associated with a corresponding pixel of a given transillumination image a corresponding quantitative value representing a quantitative measure of power loss along an optical path of a collimated light beam travelling from the illumination source, through the region of interest, to the detector is obtained. Use of calibration data in this manner allows for determination of a quantitative optical absorption map.

D. Additional Processing

In certain embodiments, denoising filters, such as Bilateral filters, are applied to the multi-angle images before performing reconstruction.

In certain embodiments, multiple sets of angular projection measurements can be obtained at multiple time points. For each set of angular projection measurements, tomographic reconstruction can be performed in order to determine a corresponding optical absorption map that represents optical absorption within the region of interest at a given time. In certain embodiments, sets of angular projection measurements can be obtained rapidly enough to provide for video rate imaging.

E. Combining SWIR Imaging with Fluorescence or Bioluminescence Tomography

In certain embodiments, the optical absorption maps obtained via the SWIR tomographic imaging approaches described herein are used as input in tomographic reconstruction processing of other imaging modalities. In particular, fluorescence and bioluminescence tomography utilize data sets corresponding to detection of light emanating from a fluorescent or bioluminescent emitter in a region of interest of a subject. The tomographic reconstruction processing employed in such optical tomographic imaging techniques typically utilizes complex forward models that describe photon propagation in diffusive media in order to infer (e.g. via solution of an inverse problem) the spatial distribution of a given probe (e.g. a fluorescent or bioluminescent emitter) using a series of measurements of light emanating from the probe within the region of the subject. Such forward models must account for absorption and multiple scattering of photons within tissue. Accordingly, the accuracy of a forward model, and, in turn, tomographic reconstructions that rely upon the forward model, rely upon accuracy with which optical properties of the tissue under study are known.

Forward models often model light propagation in diffusive media as a function of absorption at various locations within a particular region of interest. Absorption at a particular location is typically accounted for via an absorption coefficient having a value that represents the rate at which the amplitude of a light wave dissipates as it propagates. While simple forward models may be established based on an assumption of a constant, average absorption coefficient throughout the region of interest, such models fail to account for spatial variation in absorption coefficients, e.g., due to differences between and throughout different organs and tissue types, as well as other factors, such as tissue density variations. Accordingly, the accuracy of tomographic reconstructions obtained using such forward models is limited by the inherent inaccuracy of the assumption of a constant absorption coefficient.

Absorption maps that comprise a plurality of different absorption coefficients assigned to different physical locations within a region of interest can be used in more accurate forward models in order to account for spatial variation in absorption within a subject. Use of absorption maps obtained via the SWIR imaging approaches described herein provide a particularly advantageous approach. Notably, such absorption maps are obtained by direct measurement of optical properties using an optical imaging modality. Accordingly, these absorption coefficients comprise measured absorption coefficients that accurately reflect the optical properties of the locations they represent. Moreover, as these absorption coefficients are measured directly for each subject, they account for variations in optical properties that can occur for different subjects.

Absorption maps provided by non-optical imaging modalities such as micro-CT or magnetic resonance imaging do not provide this capability. For example, non-optical imaging modalities do not directly measure (or reconstruct) optical properties of a sample. Instead, non-optical imaging techniques such as MRI aid in establishing an anatomical map of the organs. To map optical properties, such as optical absorption, look-up table approaches must be used to assign predefined absorption coefficients to organs. These approaches suffer from the assumption that organ absorption values and profiles do not change from animal to animal. Moreover, the assumption that organ boundaries are truly representative of the absorptive region boundaries in optical imaging is built into these approaches.

Accordingly, optical absorption maps obtained via the SWIR imaging approaches described herein can be used to establish forward models that account for heterogeneous optical properties of tissue within the region of interest in an accurate and subject-specific fashion. Using such forward models in tomographic reconstruction procedures for other imaging modalities improves the accuracy of said tomographic reconstruction procedures and provides for improved imaging.

For example, optical absorption maps determined via the SWIR tomographic imaging approach described herein may be incorporated into forward models used in tomographic reconstruction procedures for reconstructing spatial distribution of emitters, such as fluorescent emitters and/or bioluminescent emitters, within a region of interest in a subject.

For example, in fluorescence tomography, excitation light having an excitation wavelength and produced by an excitation light source is directed to a region of interest of the subject to excite a fluorescent emitters located in the region of interest. Light emitted from the excited fluorescent emitters is detected by a detector. The excitation source may direct excitation light into the region of interest from a plurality of locations, for example by scanning a fiber, directing a beam via movable free-space optics, and other beam scanning approaches. Likewise, the detector may detect emitted light at a plurality of detection locations, for example via use of a focal plane array (FPA) detector (e.g., a CCD or CMOS camera) comprising a plurality of pixels, a fiber bundle, and other approaches. A data set comprising the measurements of the fluorescent emission for various combinations of excitation locations and detection locations can be used, along with a forward model, in tomographic reconstruction procedures to an image representing, for example, a spatial distribution of the fluorescent emitters (e.g., a spatially varying concentration) within the region of interest.

In certain embodiments, the fluorescent emitters are probes administered to the subject (e.g., by injection) prior to imaging. In certain embodiments the fluorescent emitters are expressed in endogenous species (e.g. proteins) within the region of interest.

In certain embodiments, a fluorescence tomographic imaging system may be combined with the SWIR imaging system. In this manner, subject movement/repositioning is limited between the SWIR imaging used to obtain the optical absorption map and fluorescence imaging. Depending on the wavelengths of excitation and/or emission of the fluorescent emitters used for fluorescence imaging the same source used for illumination in the SWIR imaging modality may also be used as an excitation source for fluorescence imaging and/or a single detector may be used for both SWIR and fluorescence imaging. Different sources and detectors may also be used, and, if necessary, co-aligned.

In certain embodiments, the excitation source is the same as a source of SWIR radiation used to illuminate the region of interest of the subject in the SWIR tomographic imaging approach described herein. In certain embodiments, the excitation source is different from the source of SWIR radiation used to illuminate the region of interest of the subject in the SWIR tomographic imaging approach described herein. In certain embodiments, the detector used to detect emission light is the same detector that is used to detect SWIR radiation transmitted through the region of interest in order to obtain the angular projection measurements used in determining the optical absorption maps describe herein. In certain embodiments, the detector used to detect emission light is distinct from detector that is used to detect SWIR radiation transmitted through the region of interest in order to obtain the angular projection measurements used in determining the optical absorption maps describe herein.

In certain embodiments, the excitation wavelength is the same as the wavelength of the illumination radiation used for SWIR multi-angle projection tomography. In certain embodiments, the emission wavelength (e.g., the wavelength of light emitted by the fluorescent probe) is the same as the wavelength of the illumination radiation used for SWIR multi-angle projection tomography.

The optical absorption maps determined from the SWIR tomographic imaging approach described herein may also be used to establish subject-specific forward models for use in conjunction with bioluminescence tomography. Unlike fluorescent probes, bioluminescent reporters offer the advantage of not requiring an external illumination to reach an excited state such that they emit light. In certain embodiments, the bioluminescent reporters are administered to the subject (e.g., by injection) prior to imaging. In certain embodiments, the bioluminescent reporter is endogenous to the subject.

In certain embodiments, the light emitted by one or more bioluminescent reporters located in a region of a subject is directed to a detector capable of detecting radiation at the emission wavelength in order to produce a dataset corresponding to the detected emission light.

In certain embodiments, the detector used to detect emission light from the bioluminescent emitter is the same detector that is used to detect SWIR radiation transmitted through the region of interest in order to obtain the angular projection measurements used in determining the optical absorption maps describe herein. In certain embodiments, the detector used to detect emission light from the bioluminescent emitter is distinct from detector that is used to detect SWIR radiation transmitted through the region of interest in order to obtain the angular projection measurements used in determining the optical absorption maps describe herein.

In certain embodiments, a subject-specific forward model is established using: (a) optical information collected using SWIR multi-angle projection tomography (e.g., a three dimensional absorption map) and (b) data corresponding to the detected emission light from the bioluminescent emitter. In certain embodiments, the subject-specific forward model is used to in combination with the data corresponding to the detected emission light in order to determine a tomographic representation of the spatial distribution of the bioluminescent emitter within the region of the subject. In certain embodiments the tomographic representation of the distribution of the bioluminescent emitter within the region of the subject is a map of the quantity (e.g., concentration) of the bioluminescent emitter in the region of the subject.

In certain embodiments, the emission wavelength (e.g., the wavelength of light emitted by the bioluminescent emitter) is the same as the wavelength of the illumination radiation used for SWIR multi-angle projection tomography.

In certain embodiments, the optical absorption maps obtained via the SWIR tomographic imaging approach described herein are useful with additional optical imaging modalities and measurement techniques including, but not limited to: endoscopy; fluorescence endoscopy; luminescence imaging; bioluminescence tomography, time resolved transmittance imaging; transmittance imaging; nonlinear microscopy; confocal imaging; acousto-optical imaging; photoacoustic imaging; reflectance spectroscopy; spectroscopy; coherence interferometry; interferometry; optical coherence tomography; diffuse optical tomography and fluorescence mediated molecular tomography (continuous wave, time domain frequency domain systems and early photon), and measurement of light scattering, absorption, polarization, luminescence, fluorescence lifetime, quantum yield, and quenching.

F. Applications, Emitters, and Probes

In certain embodiments, the systems and methods described herein provide for features in vivo imaging of a subject. The systems and methods allow for the recording of multiple biological processes, functions or targets. The approach described can be used to determine a number of indicia, including tracking the localization of the imaging probes (e.g. fluorescent probes) or reporters (e.g., bioluminescent reporters) in the subject over time or assessing changes or alterations in the metabolism and/or excretion of the imaging probes or reporters in the subject over time. The approach described herein can also be used to follow therapy for such diseases by imaging molecular events and biological pathways modulated by such therapy, including but not limited to determining efficacy, optimal timing, optimal dosing levels (including for individual patients or test subjects), pharmacodynamic parameters, and synergistic effects of combinations of therapy.

The systems and methods described herein can be used to help a physician, surgeon, or other medical personnel to identify and characterize areas of disease, such as arthritis, cancers, metastases or vulnerable or unstable plaque, to distinguish diseased and normal tissue, such as detecting tumor margins that are difficult to detect.

The approaches for SWIR tomographic imaging, as well as the fluorescence or bioluminescence imaging approaches using the optical absorption maps determined via the SWIR tomographic imaging approach described herein can also be used in the detection, characterization and/or determination of the localization of a disease, especially early disease, the severity of a disease or a disease-associated condition, the staging of a disease, and monitoring and guiding various therapeutic interventions, such as surgical procedures, and monitoring and/or development of drug therapy and delivery, including cell based therapies.

The systems and methods described herein can also be used in prognosis of a disease or disease condition. With respect to each of the foregoing, examples of such disease or disease conditions that can be detected or monitored (before, during or after therapy) include inflammation (for example, inflammation caused by arthritis, for example, rheumatoid arthritis), cancer (for example, colorectal, ovarian, lung, breast, prostate, cervical, testicular, skin, brain, gastrointestinal, pancreatic, liver, kidney, bladder, stomach, leukemia, mouth, esophageal, bone, including metastases), cardiovascular disease (for example, atherosclerosis and inflammatory conditions of blood vessels, ischemia, stroke, thrombosis, disseminated intravascular coagulation), dermatologic disease (for example, Kaposi's Sarcoma, psoriasis, allergic dermatitis), ophthalmic disease (for example, macular degeneration, diabetic retinopathy), infectious disease (for example, bacterial, viral, fungal and parasitic infections, including Acquired Immunodeficiency Syndrome, Malaria, Chagas Disease, Schistosomiasis), immunologic disease (for example, an autoimmune disorder, lymphoma, multiple sclerosis, rheumatoid arthritis, diabetes mellitus, lupus erythematosis, myasthenia gravis, Graves disease), central nervous system disease (for example, a neurodegenerative disease, such as Parkinson's disease or Alzheimer's disease, Huntington's Disease, amyotrophic lateral sclerosis, prion disease), inherited diseases, metabolic diseases, environmental diseases (for example, lead, mercury and radioactive poisoning, skin cancer), bone-related disease (for example, osteoporosis, primary and metastatic bone tumors, osteoarthritis), neurodegenerative disease, and surgery-related complications (such as graft rejection, organ rejection, alterations in wound healing, fibrosis or other complications related to surgical implants). The systems and methods described herein can therefore be used, for example, to determine the presence of tumor cells and localization and metastases of tumor cells, the presence and localization of inflammation, including the presence of activated macrophages, for instance in atherosclerosis or arthritis, the presence and localization of vascular disease including areas at risk for acute occlusion (e.g., vulnerable plaques) in coronary and peripheral arteries, regions of expanding aneurysms, unstable plaque in carotid arteries, and ischemic areas, and stent thrombosis. The systems and methods described herein can also be used in identification and evaluation of cell death, injury, apoptosis, necrosis, hypoxia and angiogenesis. The systems and methods described herein can also be used in for monitoring trafficking and localization of certain cell types, including T-cells, tumor cells, immune cells, stem cells, and other cell types. In particular, this method may be used to monitor cell based therapies. The systems and methods described herein can also be used as part of photodynamic therapy, including imaging, photoactivation and therapy monitoring.

In certain embodiments, the systems and methods described herein can be used to image endogenous fluorescence in a subject. For example, a gene encoding a fluorescent protein, such as green, red or infrared fluorescent protein, can be included adjacent to a gene of interest that is to be expressed in an animal or human subject using standard gene therapy and transgenic techniques. The expression of the gene of interest can be determined indirectly by imaging the fluorescent protein. If this protein is expressed, then the gene of interest has also been expressed. Fluorescence properties of endogenous fluorescent proteins are described in Giepmans et al., *Science*, 312: 217-224, 2006; Shaner et al., *Nature Methods* 2:905-909, 2005; and Zhang et al., *Nat. Rev. Mol. Biol.* 3: 906-918, 2002; Ai et al., *Biochemistry* 46:5904-5910, 2007; Shaner et al., *Nat. Biotech* 22:1567-1572, 2004; Campbell et al., *Proc. Nat. Acad. Sci.* 99:7877-7882, 2002; Heikal et al. *Proc. Nat. Acad. Sci.* 97:11996-12001, 2000; Baird et al., *Proc. Nat. Acad. Sci.* 97:11984-11989, 2000; Tsien, *Ann. Rev. Biochem.* 67:509-44, 1998; Heim et al., *Curr. Biol.* 6:178-182, 1996; Cubitt et al., *Trends Biochem Sci.* 11:448-455, 1995; Heim et al., *Proc. Nat. Acad. Sci* 91:12501-12504, 1994; the relevant text incorporated by reference herein.

G. Computer Systems and Network Environment

Figure 5:
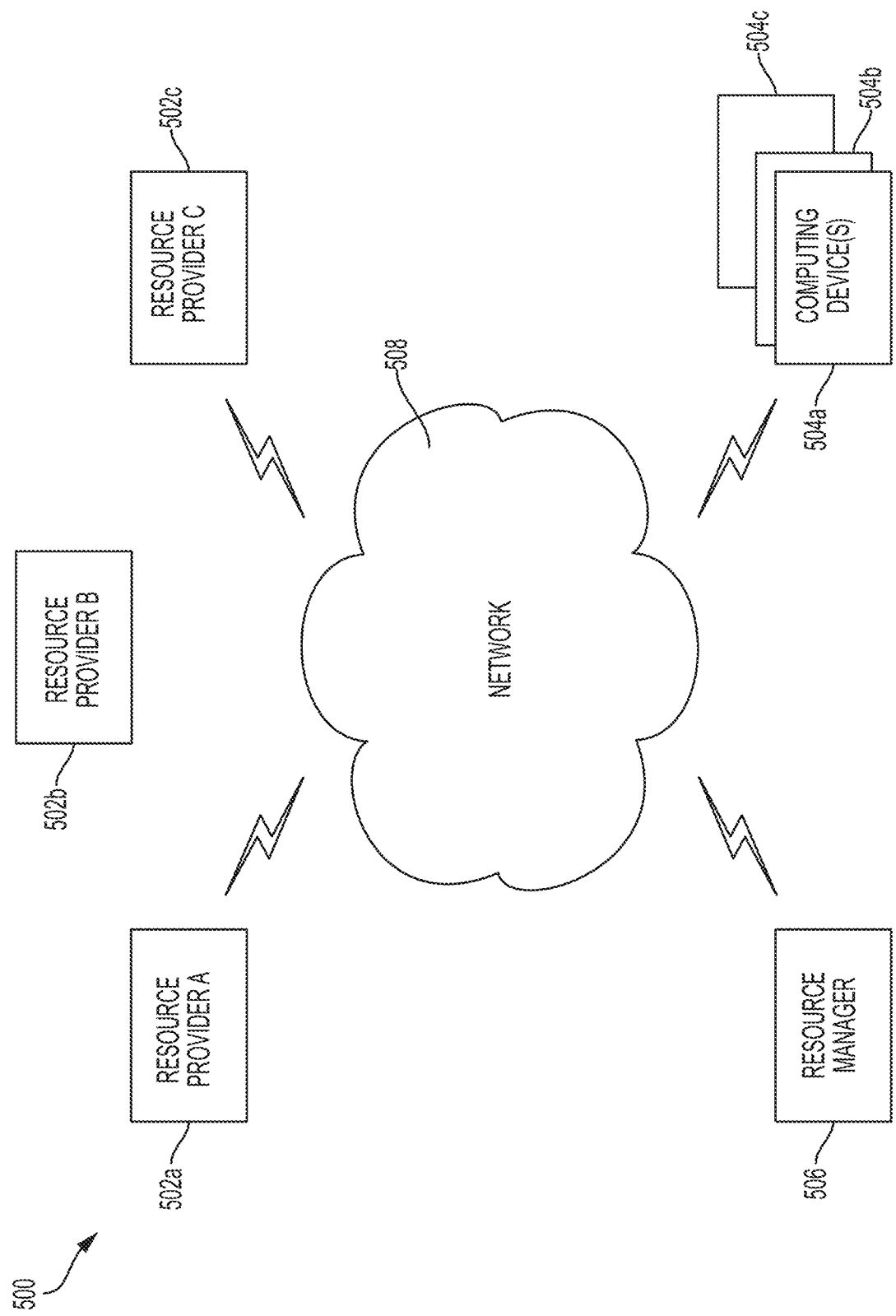
FIG. 5 is a block diagram of an example network environment for use in the methods and systems described herein, according to an illustrative embodiment.

As shown in FIG. 5, an implementation of a network environment 500 for use in providing systems and methods for multi-angle SWIR tomography as described herein. In brief overview, referring now to FIG. 5, a block diagram of an exemplary cloud computing environment 500 is shown and described. The cloud computing environment 500 may include one or more resource providers 502a, 502b, 502c (collectively, 502). Each resource provider 502 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 502 may be connected to any other resource provider 502 in the cloud computing environment 500. In some implementations, the resource providers 502 may be connected over a computer network 508. Each resource provider 502 may be connected to one or more computing device 504a, 504b, 504c (collectively, 504), over the computer network 508.

The cloud computing environment 500 may include a resource manager 506. The resource manager 506 may be connected to the resource providers 502 and the computing devices 504 over the computer network 508. In some implementations, the resource manager 506 may facilitate the provision of computing resources by one or more resource providers 502 to one or more computing devices 504. The resource manager 506 may receive a request for a computing resource from a particular computing device 504. The resource manager 506 may identify one or more resource providers 502 capable of providing the computing resource requested by the computing device 504. The resource manager 506 may select a resource provider 502 to provide the computing resource. The resource manager 506 may facilitate a connection between the resource provider 502 and a particular computing device 504. In some implementations, the resource manager 506 may establish a connection between a particular resource provider 502 and a particular computing device 504. In some implementations, the resource manager 506 may redirect a particular computing device 504 to a particular resource provider 502 with the requested computing resource.

Figure 6:
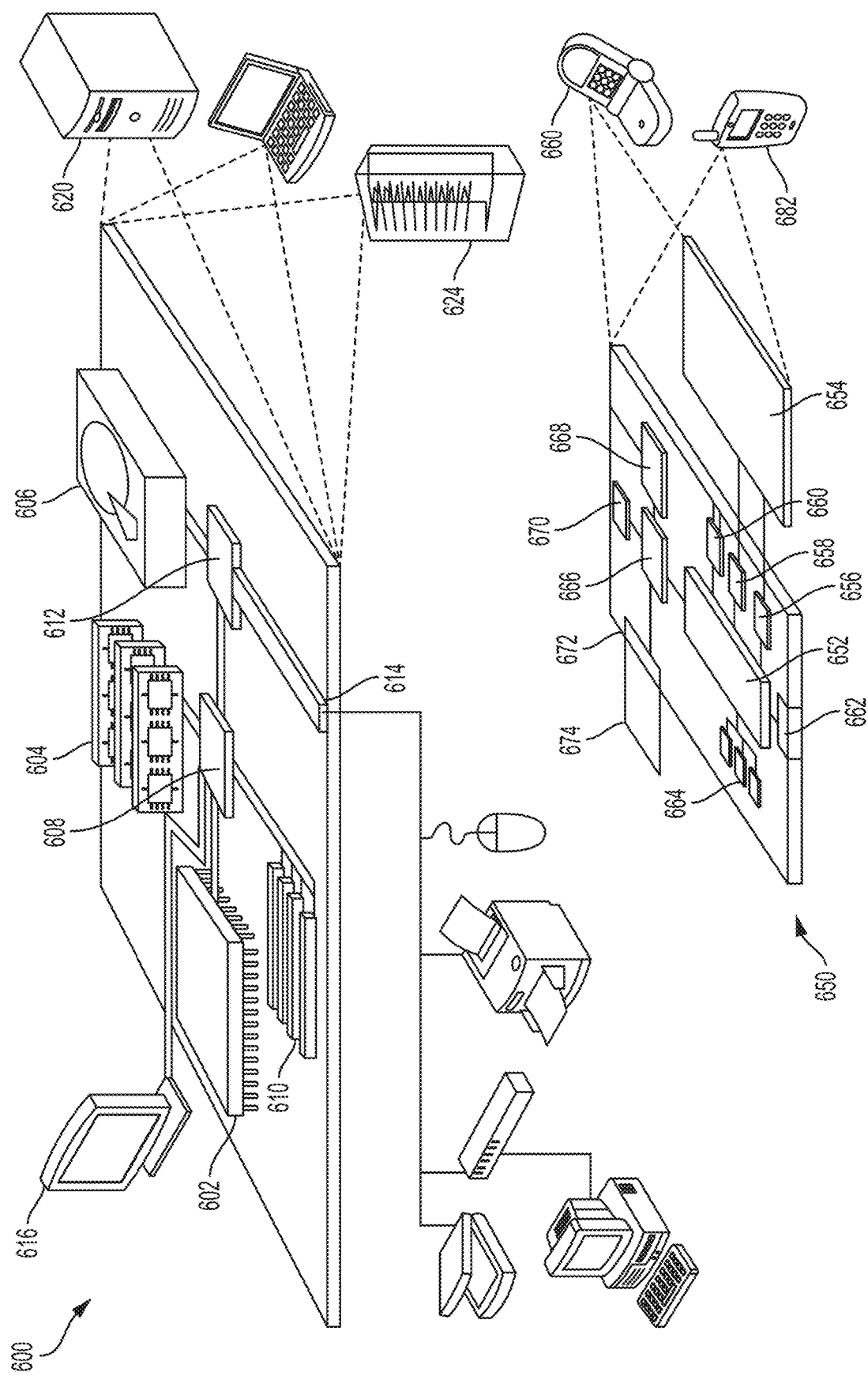
FIG. 6 is a block diagram of an example computing device and an example mobile computing device, for use in illustrative embodiments of the invention.

FIG. 6 shows an example of a computing device 600 and a mobile computing device 650 that can be used to implement the techniques described in this disclosure. The computing device 600 is intended to represent various forms of digital computers, such as laptops, desktops, workstations, personal digital assistants, servers, blade servers, mainframes, and other appropriate computers. The mobile computing device 650 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 600 includes a processor 602, a memory 604, a storage device 606, a high-speed interface 608 connecting to the memory 604 and multiple high-speed expansion ports 610, and a low-speed interface 612 connecting to a low-speed expansion port 614 and the storage device 606. Each of the processor 602, the memory 604, the storage device 606, the high-speed interface 608, the high-speed expansion ports 610, and the low-speed interface 612, are interconnected using various busses, and may be mounted on a common motherboard or in other manners as appropriate. The processor 602 can process instructions for execution within the computing device 600, including instructions stored in the memory 604 or on the storage device 606 to display graphical information for a GUI on an external input/output device, such as a display 616 coupled to the high-speed interface 608. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system). Thus, as the term is used herein, where a plurality of functions are described as being performed by "a processor", this encompasses embodiments wherein the plurality of functions are performed by any number of processors (one or more) of any number of computing devices (one or more). Furthermore, where a function is described as being performed by "a processor", this encompasses embodiments wherein the function is performed by any number of processors (one or more) of any number of computing devices (one or more) (e.g., in a distributed computing system).

The memory 604 stores information within the computing device 600. In some implementations, the memory 604 is a volatile memory unit or units. In some implementations, the memory 604 is a non-volatile memory unit or units. The memory 604 may also be another form of computer-readable medium, such as a magnetic or optical disk.

The storage device 606 is capable of providing mass storage for the computing device 600. In some implementations, the storage device 606 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 602), perform one or more methods, such as those described above. The instructions can also be stored by one or more storage devices such as computer- or machine-readable mediums (for example, the memory 604, the storage device 606, or memory on the processor 602).

The high-speed interface 608 manages bandwidth-intensive operations for the computing device 600, while the low-speed interface 612 manages lower bandwidth-intensive operations. Such allocation of functions is an example only. In some implementations, the high-speed interface 608 is coupled to the memory 604, the display 616 (e.g., through a graphics processor or accelerator), and to the high-speed expansion ports 610, which may accept various expansion cards (not shown). In the implementation, the low-speed interface 612 is coupled to the storage device 606 and the low-speed expansion port 614. The low-speed expansion port 614, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 600 may be implemented in a number of different forms, as shown in the figure. For example, it may be implemented as a standard server 620, or multiple times in a group of such servers. In addition, it may be implemented in a personal computer such as a laptop computer 622. It may also be implemented as part of a rack server system 624. Alternatively, components from the computing device 600 may be combined with other components in a mobile device (not shown), such as a mobile computing device 650. Each of such devices may contain one or more of the computing device 600 and the mobile computing device 650, and an entire system may be made up of multiple computing devices communicating with each other.

The mobile computing device 650 includes a processor 652, a memory 664, an input/output device such as a display 654, a communication interface 666, and a transceiver 668, among other components. The mobile computing device 650 may also be provided with a storage device, such as a micro-drive or other device, to provide additional storage. Each of the processor 652, the memory 664, the display 654, the communication interface 666, and the transceiver 668, are interconnected using various buses, and several of the components may be mounted on a common motherboard or in other manners as appropriate.

The processor 652 can execute instructions within the mobile computing device 650, including instructions stored in the memory 664. The processor 652 may be implemented as a chipset of chips that include separate and multiple analog and digital processors. The processor 652 may provide, for example, for coordination of the other components of the mobile computing device 650, such as control of user interfaces, applications run by the mobile computing device 650, and wireless communication by the mobile computing device 650.

The processor 652 may communicate with a user through a control interface 658 and a display interface 656 coupled to the display 654. The display 654 may be, for example, a TFT (Thin-Film-Transistor Liquid Crystal Display) display or an OLED (Organic Light Emitting Diode) display, or other appropriate display technology. The display interface 656 may comprise appropriate circuitry for driving the display 654 to present graphical and other information to a user. The control interface 658 may receive commands from a user and convert them for submission to the processor 652. In addition, an external interface 662 may provide communication with the processor 652, so as to enable near area communication of the mobile computing device 650 with other devices. The external interface 662 may provide, for example, for wired communication in some implementations, or for wireless communication in other implementations, and multiple interfaces may also be used.

The memory 664 stores information within the mobile computing device 650. The memory 664 can be implemented as one or more of a computer-readable medium or media, a volatile memory unit or units, or a non-volatile memory unit or units. An expansion memory 674 may also be provided and connected to the mobile computing device 650 through an expansion interface 672, which may include, for example, a SIMM (Single In Line Memory Module) card interface. The expansion memory 674 may provide extra storage space for the mobile computing device 650, or may also store applications or other information for the mobile computing device 650. Specifically, the expansion memory 674 may include instructions to carry out or supplement the processes described above, and may include secure information also. Thus, for example, the expansion memory 674 may be provide as a security module for the mobile computing device 650, and may be programmed with instructions that permit secure use of the mobile computing device 650. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier. that the instructions, when executed by one or more processing devices (for example, processor 652), perform one or more methods, such as those described above. The instructions can also be stored by one or more storage devices, such as one or more computer- or machine-readable mediums (for example, the memory 664, the expansion memory 674, or memory on the processor 652). In some implementations, the instructions can be received in a propagated signal, for example, over the transceiver 668 or the external interface 662.

The mobile computing device 650 may communicate wirelessly through the communication interface 666, which may include digital signal processing circuitry where necessary. The communication interface 666 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 668 using a radio-frequency. In addition, short-range communication may occur, such as using a Bluetooth®, Wi-Fi™, or other such transceiver (not shown). In addition, a GPS (Global Positioning System) receiver module 670 may provide additional navigation- and location-related wireless data to the mobile computing device 650, which may be used as appropriate by applications running on the mobile computing device 650.

The mobile computing device 650 may also communicate audibly using an audio codec 660, which may receive spoken information from a user and convert it to usable digital information. The audio codec 660 may likewise generate audible sound for a user, such as through a speaker, e.g., in a handset of the mobile computing device 650. Such sound may include sound from voice telephone calls, may include recorded sound (e.g., voice messages, music files, etc.) and may also include sound generated by applications operating on the mobile computing device 650.

The mobile computing device 650 may be implemented in a number of different forms, as shown in the figure. For example, it may be implemented as a cellular telephone 680. It may also be implemented as part of a smart-phone 682, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

Elements of different implementations described herein may be combined to form other implementations not specifically set forth above. Elements may be left out of the processes, computer programs, databases, etc. described herein without adversely affecting their operation. In addition, the logic flows depicted in the figures do not require the particular order shown, or sequential order, to achieve desirable results. Various separate elements may be combined into one or more individual elements to perform the functions described herein.

Throughout the description, where apparatus and systems are described as having, including, or comprising specific components, or where processes and methods are described as having, including, or comprising specific steps, it is contemplated that, additionally, there are apparatus, and systems of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

While apparatus, systems, and methods have been particularly shown and described with reference to specific preferred embodiments, it should be understood by those skilled in the art that various changes in form and detail may be made therein without departing from the spirit and scope of the invention as defined by the appended claims.

What is claimed is:

1. A system for creating an optical tomographic image of a region of interest of a subject, the system comprising:
   (a) a sample stage configured for mounting the subject, the sample stage configured to be in a fixed position in a first condition and to rotate about an axis passing through a center of the sample stage in a second condition;
   (b) a first source configured to output illumination radiation configured to be directed through a collimator and a beam expander into the region of interest of the subject, wherein the radiation is short-wave infrared radiation (SWIR) having a wavelength from 1000 nm to 1500 nm, the first source is configured to be mounted on a gantry that rotates about the subject in the first condition about an axis that is parallel to the axis passing through a center of the sample stage, and the gantry is fixed in the second condition in which the stage rotates;
   (c) a first detector configured to detect radiation from the first source, wherein the detected radiation is radiation transmitted through the region of interest of the subject, the first detector is configured to be mounted on the gantry that rotates about the subject in the first condition, and the gantry is fixed in the second condition in which the stage rotates;
   (d) a memory, configured to store a set of instructions; and
   (e) a processor configured to execute the set of instructions, wherein the set of instructions when executed by the processor in either the first condition or the second condition:
   position the sample stage, the first source, and the first detector with respect to one another so that the first source is positioned to illuminate the region of interest at a plurality of illumination angles and so that the first detector is positioned to detect radiation transmitted through the region of interest at a plurality of detection angles, wherein each of the plurality of detection angles correspond to each of the plurality of illumination angles, and
   determine a value of a power of the illumination radiation at each of the plurality of illumination angles, determine a value of a power of the detected radiation at each of the plurality of detecting angles, obtain a plurality of angular projection measurements, wherein each of the plurality of angular projection measurements comprises determining a ratio of the value of a power of the illumination radiation determined at each of the plurality of illumination angles to the power of the illumination radiation determined at each of the plurality of illumination angles, and determine an optical absorption map of the region of interest using data corresponding to the plurality of angular projection measurements, and the processor is further configured to execute the set of instructions, the set of instructions cause the processor to determine a tomographic reconstruction of the optical absorption map of the region of interest.

2. The system of claim 1, wherein the set of instructions cause the processor to invert a projection model of radiation transmission from the first source, through the region of interest of the subject, to the first detector at each of the plurality of illumination angles and corresponding detection angles to determine the optical absorption map of the region of interest.

3. The system of claim 2, wherein inverting the projection model comprises applying an inverse operator of the projection model to a plurality of observation values determined using the data corresponding to the plurality of angular projection measurements, thereby determining the optical absorption map of the region of interest.

4. The system of claim 2, wherein the projection model is a discretized model that relates, for each of the plurality of angular measurements, (i) a value corresponding to an intensity of the detected radiation at the angular measurement to (ii) a plurality of optical absorption coefficients, each representing optical absorption at a specific point within the region of interest.

5. The system of claim 4, wherein the set of instructions cause the processor to determine the optical absorption map by applying a discretized version of an inverse operator of the projection model to determine, for each of a plurality of discretized locations, a corresponding value of the optical absorption coefficient, wherein the discretized inverse operator of the projection model relates, for each of a plurality of discretized locations representing physical locations in the region of interest, a value of an optical absorption coefficient at the location to at least a portion of a plurality of observation values determined using the data corresponding to the angular projection measurements.

6. The system of claim 1, wherein the set of instructions cause the processor to determine the optical absorption map using the data corresponding to the plurality of angular projection measurements and calibration data, wherein the optical absorption map is quantitative.

7. The system of claim 6, wherein the calibration data comprises at least one member selected from the group consisting of:
   data corresponding to a power of the source;
   data corresponding to measurement(s) of a radiometric configuration of the system; and
   data corresponding to an intensity response of the detector.

8. The system of claim 1, wherein the set of instructions cause the processor to obtain a measurement of one or more boundaries representing a surface of the subject about the region of interest, wherein the set of instructions, when executed by the processor, cause the processor to determine the optical absorption map using the measurement of the one or more boundaries.

9. The system of claim 1, wherein the set of instructions cause the processor to apply one or more denoising filters to the data corresponding to the plurality of angular projection measurements.

10. The system of claim 1, wherein the region of interest comprises one or more anatomical organs and the set of instructions cause the processor to process the optical absorption map to automatically localize the one or more anatomical organs in the optical absorption map.

11. The system of claim 1, wherein the sample stage, first source, and first detector are operable to allow recording at each of a plurality of time points, a corresponding set of a plurality of angular projection measurements, and wherein the set of instructions cause the processor to:

for each of the plurality of time points, determine a corresponding optical absorption map of the region of interest using data corresponding to the corresponding set of the plurality of angular projection measurements, thereby determining a plurality of optical absorption maps representing optical absorption in the region of interest at each of the plurality of time points.

12. The system of claim 11, wherein a temporal separation between each of the plurality of time points is sufficiently small so as to provide video rate images of optical absorption in the region of the subject.

13. The system of claim 1, wherein the set of instructions cause the processor to use the determined optical absorption map to obtain a tomographic representation of a distribution of a fluorescent and/or bioluminescent emitter within the region of the subject.

14. The system of claim 1,
wherein the first source is an excitation source aligned to direct the SWIR configured to be output as excitation light into the region of interest of the subject, the excitation light having a wavelength corresponding to an excitation wavelength of a fluorescent emitter present in the region of interest,
wherein the first detector is a fluorescence detector aligned to detect fluorescent light emitted from the fluorescent emitter in the region of interest, wherein the fluorescence detector is responsive to light having a wavelength corresponding to an emission wavelength of the fluorescent emitter present in the region of interest, and
wherein the set of instructions cause the processor to determine a tomographic representation of a distribution of the fluorescent emitter in the region of interest using data corresponding to the detected fluorescent light and the determined optical absorption map.

15. The system of claim 14, wherein the excitation source is operable direct the excitation into the region of interest from a plurality of different excitation source positions.

16. The system of claim 14, wherein the fluorescence detector is operable to detect fluorescent light emitted from the region of interest at a plurality of different fluorescent detector positions.

17. The system of claim 14, wherein the set of instructions cause the processor to determine the tomographic representation of the distribution of the fluorescent emitter by inverting a forward model that describes (i) excitation light propagation from a point corresponding to an excitation source position to a point corresponding to a position of a fluorescent emitter in the region of interest and (ii) emission light propagation from the position of the fluorescent emitter to a point corresponding to a fluorescence detector position.

18. The system of claim 17, wherein the set of instructions cause the processor to use the determined optical absorption map in the forward model.

19. The system of claim 14, wherein the set of instructions cause the processor to determine a map of a concentration of the fluorescent emitter in the region of interest using data corresponding to the detected fluorescent light and the determined optical absorption map.

* * * * *

UNITED STATES PATENT AND TRADEMARK OFFICE
CERTIFICATE OF CORRECTION

| | | |
|---|---|---|
| PATENT NO. | : 11,989,803 B2 | Page 1 of 1 |
| APPLICATION NO. | : 16/339445 | |
| DATED | : May 21, 2024 | |
| INVENTOR(S) | : Ali Behrooz | |

It is certified that error appears in the above-identified patent and that said Letters Patent is hereby corrected as shown below:

On the Title Page

Assignee Item (73):
Please delete:
"PerkinElmer Health Sciences, Inc."
And insert:
--Revvity Health Sciences, Inc.--

Signed and Sealed this
Eleventh Day of February, 2025

Coke Morgan Stewart
*Acting Director of the United States Patent and Trademark Office*